US012178807B2

United States Patent
Liu

(10) Patent No.: US 12,178,807 B2
(45) Date of Patent: Dec. 31, 2024

(54) MACROCYCLIC TYROSINE KINASE INHIBITOR AND USES THEREOF

(71) Applicant: XUANZHU BIOPHARMACEUTICAL CO., LTD., Shijiazhuang (CN)

(72) Inventor: Bin Liu, Jinan (CN)

(73) Assignee: XUANZHU BIOPHARMACEUTICAL CO., LTD., Shijiazhuang (CN)

( * ) Notice: Subject to any disclaimer, the term of this patent is extended or adjusted under 35 U.S.C. 154(b) by 828 days.

(21) Appl. No.: 17/292,084

(22) PCT Filed: Nov. 8, 2019

(86) PCT No.: PCT/CN2019/116459
§ 371 (c)(1),
(2) Date: May 7, 2021

(87) PCT Pub. No.: WO2020/094112
PCT Pub. Date: May 14, 2020

(65) Prior Publication Data
US 2021/0401814 A1    Dec. 30, 2021

(30) Foreign Application Priority Data

Nov. 9, 2018 (CN) .................. 201811328658.X
Jan. 30, 2019 (CN) .................. 201910091922.0

(51) Int. Cl.
| | | |
|---|---|---|
| *A61K 31/439* | (2006.01) | |
| *A61K 31/122* | (2006.01) | |
| *A61K 31/5377* | (2006.01) | |
| *A61K 31/675* | (2006.01) | |
| *A61K 38/13* | (2006.01) | |
| *A61P 35/00* | (2006.01) | |
| *C07D 471/22* | (2006.01) | |
| *C07D 498/22* | (2006.01) | |

(52) U.S. Cl.
CPC .......... *A61K 31/439* (2013.01); *A61K 31/122* (2013.01); *A61K 31/5377* (2013.01); *A61K 31/675* (2013.01); *A61K 38/13* (2013.01); *A61P 35/00* (2018.01); *C07D 471/22* (2013.01); *C07D 498/22* (2013.01)

(58) Field of Classification Search
CPC ................ A61K 31/439; A61K 31/122; A61K 31/5377; A61K 31/675; A61K 38/13; A61P 35/00; C07D 471/22; C07D 498/22
USPC ......................................................... 514/281
See application file for complete search history.

(56) References Cited

U.S. PATENT DOCUMENTS

2014/0206683 A1    7/2014    Hoflack et al.

FOREIGN PATENT DOCUMENTS

| CN | 102143750 A | 8/2011 | |
|---|---|---|---|
| CN | 103748099 A | 4/2014 | |
| CN | 106170289 A | 11/2016 | |
| RU | 2622104 C2 | 6/2017 | |
| WO | WO 2010/028116 A1 | 3/2010 | |
| WO | WO 2012/156756 A2 | 11/2012 | |
| WO | WO 2015/112806 A2 | 7/2015 | |
| WO | WO-2018081417 A2 * | 5/2018 | ........... A61K 31/519 |
| WO | WO 2019/094143 A1 | 5/2019 | |

OTHER PUBLICATIONS

English Translation of Chinese International Search Report mailed Dec. 19, 2019, for PCT/CN2019/116459, 4 pages.
English Translation of Russian Office Action issued Mar. 21, 2022, for Russian Application No. 2021116442, 29 pages.
English Translation of Russian Search Report issued Mar. 21, 2022, for Russian Application No. 2021116442, 4 pages.

* cited by examiner

*Primary Examiner* — Yevgeny Valenrod
(74) *Attorney, Agent, or Firm* — Morgan, Lewis & Bockius LLP

(57) ABSTRACT

The present invention belongs to the technical field of medicine, and relates to a macrocyclic tyrosine kinase inhibitor and the uses thereof. Specifically, the invention relates to a compound of general formula (I) or a pharmaceutically acceptable salt, ester or stereoisomer thereof, a preparation method therefor, a pharmaceutical formulation or a pharmaceutical composition containing same, and medical uses thereof.

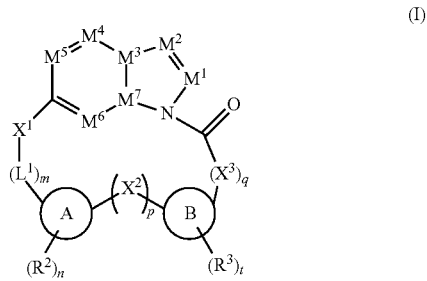

10 Claims, No Drawings

MACROCYCLIC TYROSINE KINASE INHIBITOR AND USES THEREOF

CROSS-REFERENCES TO RELATED APPLICATIONS

This application is a U.S. national phase application of PCT Application No. PCT/CN2019/116459 filed on Nov. 8, 2019, which claims priority to Chinese Patent Application No. 201811328658.X filed in China on Nov. 9, 2018, and Chinese Patent Application No. 201910091922.0 filed in China on Jan. 30, 2019, the disclosures of which are incorporated herein by reference in their entirety.

TECHNICAL FIELD

The present invention belongs to the technical field of medicine, and particularly relates to a macrocyclic tyrosine kinase inhibitor compound or a pharmaceutically acceptable salt, ester or stereoisomer thereof. The tyrosine kinase is one or more of TRK, ALK and/or ROS1. The present invention further relates to a pharmaceutical composition or formulation containing the compound or the pharmaceutically acceptable salt, ester or stereoisomer thereof, a method for preparing the compound or the pharmaceutically acceptable salt, ester or stereoisomer thereof, and uses of the compound or the pharmaceutically acceptable salt, ester or stereoisomer thereof.

BACKGROUND

Cancer, also known as malignant tumor, is a serious threat to human health and life. In 2004, 7.4 million people died from cancer worldwide. In 2008, the third national survey on causes of death in China shows that the cancer death rate in China has increased by about 80% in the last 30 years, and nearly 2 million people died from cancer every year, which lead to a very severe situation.

Molecular targeted therapy has been a major breakthrough in cancer treatment in recent years. Compared with traditional treatment means such as surgery, radiotherapy and chemotherapy, the molecular targeted therapy breaks new ground for cancer treatment with its high specificity and relatively low toxic side effects, and gradually serves as a standard treatment scheme for patients with advanced cancer. Protein kinases, a large field of targeted therapy, are key regulators for cell growth, proliferation and survival, and both genetic and epigenetic alterations may lead to the occurrence of cancer.

Anaplastic lymphoma kinase (ALK) was named after its first discovery in the anaplastic large cell lymphoma AMS3 cell line. EML4 belongs to echinoderm microtubule-associated protein family, and consists of an N-terminus base region, a hydrophobic echinoderm microtubule-associated protein region and a WD repeat region. It has been reported that an EML4-ALK fusion gene is related to the formation of tumors, and an N-terminus base region plays the most important role. Soda et al. (2007) reported the EML4-ALK gene fusion in non-small cell lung cancer (NSCLC) for the first time which is a result of inversion of the short arm of chromosome 2, with EML4 fused to an intracellular ALK kinase region at the N-terminus. EML4-ALK fusion sites are various, and at least 8 EML4-ALK mutants are formed. ALK mutations have been found in a variety of cancers, including anaplastic large cell lymphoma (ALCL), non-small cell lung cancer, inflammatory myofibroblast tumor, colorectal cancer, breast cancer and several others.

ROS1 is also a tyrosine kinase receptor that has attracted much attention. ROS1 is located at region 6q21 and the full length cDNA thereof contains 44 exons. ROS1 encodes 2347 amino acids with a molecular weight of 259 kDa. The basic structure of ROS1 consists of an extramembrane region (amino acids 1-1861), a transmembrane region (amino acids 1862-1882) and a tyrosine kinase active region (amino acids 1883-2347) within the membrane. The first proto-oncogene fusion site of ROS1 (FIG-ROS1) is found in glioblastoma, and an intermediate deletion of 240 bases on 6q21 results in the expression of FIG-ROS1 fusion protein, which activates the activity of tyrosine kinase. ROS1 mutations have also been found in a variety of cancers, including glioblastoma, non-small cell lung cancer, colorectal cancer, breast cancer and the like.

Trks are a family of nerve growth factor-activated tyrosine kinases, including three subtypes TrkA, TrkB and TrkC, and are encoded by NTRK1 (neuronal receptor tyrosine kinase 1), NTRK2 and NTRK3 genes, respectively. After Trk kinases are phosphorylated, downstream signal molecules can be activated, thereby playing roles in regulating cell proliferation, differentiation, metabolism, apoptosis and the like.

The NTRK gene can be fused with other genes, which causes the high expression of Trk kinases or continuous increase of the activity of Trk kinases, and finally may lead to cancer. NTRK gene fusion occurs in a variety of adult and pediatric solid tumors, including breast cancer, colorectal cancer, non-small cell lung cancer and various sarcomas.

The above three tyrosine kinases have strong homology. The ROS1 gene and the ALK gene have 49% homology in the tyrosine kinase region sequence, and have a high 77% homology in ATP binding site of kinase catalytic region. The kinase region sequences of TRK A/B/C have over 80% homology. The TRK A gene, the ROS1 gene and the ALK gene have about 40% homology in the tyrosine kinase region sequence. The marketed ALK inhibitor Crizotinib has ROS1 and TRK inhibitory activities simultaneously, and the TRK inhibitor Entrectinib also has ALK and ROS1 inhibitory activities.

At present, both the marketed ALK/ROS1 inhibitors and the NTRK inhibitors filed NDA in 2017 have appeared drug resistance during long-term medication, mainly because the amino acid sequence of the kinase protein is changed due to gene mutation, such as common mutation sites in ALK kinases including L1196M, L1152R, G1202R, G1269A, 1151Tins, S1206Y, C1156Y, F1174L and the like, common mutation sites in ROS1 kinases including G2032R, D2033N, S1986F, L2026M, L1951R and the like, and common mutation sites in NTRK kinases including G595R, G623R, G667C, G623E, L686M and the like. Therefore, the development of an anti-tumor drug which has strong efficacy and low toxicity and can solve drug resistance has very important clinical value and significance.

SUMMARY OF THE INVENTION

In order to solve the aforementioned problem, the present invention provides a compound with a tyrosine kinase receptor inhibition effect or a pharmaceutically acceptable salt, ester or stereoisomer thereof. The tyrosine kinase receptor may be one or more of TRK, ALK and ROS1. In addition, the compound has better inhibitory activity on one or more of TrkA, TrkB and TrkC kinases, and has higher exposure and bioavailability in organisms.

In order to solve the aforementioned problem, the present invention also provides a method for treating a cancer disease mediated by one or more tyrosine kinase receptors of TRK, ALK and ROS1 using the compound of the present invention, or the pharmaceutically acceptable salt, ester or stereoisomer thereof. The cancer disease may have developed resistance to one or more existing therapeutically active agents, and the resistance may be caused by a mutation in the gene encoding targets. Preferably, the mutant gene is an NTRK gene.

In one aspect, the present application provides a compound of general formula (I) or a pharmaceutically acceptable salt, ester or stereoisomer thereof,

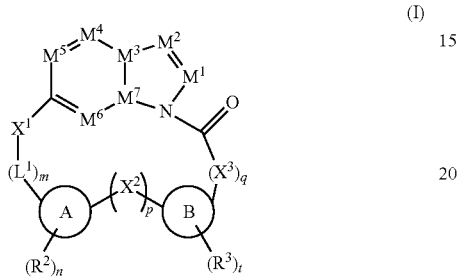

(I)

wherein:
- $M^1$, $M^2$, $M^3$, $M^4$, $M^5$, $M^6$ and $M^7$ are each independently selected from C, $C(R^1)$ and N;
- $X^1$, $X^2$, $X^3$ and L, when present, are each independently selected from —$C(R^5)(R^6)$—, —$N(R^4)$—, —O—, —S—, —S(O)— and —$S(O)_2$—;
- ring A is selected from 3-10 membered cycloalkyl, 3-10 membered heterocyclyl, 6-8 membered monoaryl, 8-10 membered fused aryl, 5-10 membered monoheteroaryl and 8-10 membered fused heteroaryl;
- ring B is absent or selected from 3-10 membered cycloalkyl and 3-10 membered heterocyclyl, and when ring B is absent, $X^2$ and $X^3$ are directly connected by a chemical bond;
- $R^1$, $R^2$, $R^3$, $R^5$ and $R^6$, when present, are each independently selected from hydrogen, halogen, nitro, cyano and the following groups optionally substituted with one or more $Q^1$: $C_{1-6}$ alkyl, $C_{2-6}$ alkenyl, $C_{2-6}$ alkynyl, —$OR^a$, —$SR^a$, —$NR^aR^b$, —$C(O)R^a$, —$C(O)OR^a$, —$OC(O)R^a$, —$OC(O)OR^a$, —$OC(O)NR^aR^b$, —$C(O)NR^aR^b$, —$NR^aC(O)R^b$, —$NR^aC(O)OR^b$, —$NR^aC(O)NR^aR^b$, —$S(O)R^a$, —$S(O)OR^a$, —$OS(O)R^a$, —$OS(O)OR^a$, —$OS(O)NR^aR^b$, —$S(O)NR^aR^b$, —$NR^aS(O)R^b$, —$NR^aS(O)OR^b$, —$NR^aS(O)NR^aR^b$, —$S(O)_2R^a$, —$S(O)_2OR^a$, —$OS(O)_2R^a$, —$OS(O)_2OR^a$, —$OS(O)_2NR^aR^b$, —$S(O)_2NR^aR^b$, —$NR^aS(O)_2R^b$, —$NR^aS(O)_2OR^b$, —$NR^aS(O)_2NR^aR^b$, 3-10 membered cycloalkyl, 3-10 membered heterocyclyl, 6-10 membered aryl and 5-10 membered heteroaryl; $Q^1$, when present, is independently selected from hydroxy, amino, halogen, nitro, cyano, $C_{1-6}$ alkyl, $C_{1-6}$ alkoxy, $C_{1-6}$ alkylamino, di($C_{1-6}$ alkyl)amino, halo $C_{1-6}$ alkyl, hydroxy $C_{1-6}$ alkyl, amino $C_{1-6}$ alkyl, halo $C_{1-6}$ alkoxy, 3-10 membered cycloalkyl, 3-10 membered heterocyclyl, 6-10 membered aryl and 5-10 membered heteroaryl;
- $R^4$, when present, is independently selected from hydrogen and the following groups optionally substituted with one or more $Q^2$: $C_{1-6}$ alkyl, $C_{2-6}$ alkenyl, $C_{2-6}$ alkynyl, —$C(O)R^a$, —$C(O)OR^a$, —$C(O)NR^aR^b$, —$S(O)R^a$, —$S(O)OR^a$, —$S(O)NR^aR^b$, —$S(O)_2R^a$, —$S(O)_2OR^a$, —$S(O)_2NR^aR^b$, 3-10 membered cycloalkyl, 3-10 membered heterocyclyl, 6-10 membered aryl and 5-10 membered heteroaryl; $Q^2$, when present, is independently selected from hydroxy, amino, halogen, nitro, cyano, $C_{1-6}$ alkyl, $C_{1-6}$ alkoxy, $C_{1-6}$ alkylamino, di($C_{1-6}$ alkyl)amino, halo $C_{1-6}$ alkyl, hydroxy $C_{1-6}$ alkyl, amino $C_{1-6}$ alkyl, halo $C_{1-6}$ alkoxy, 3-10 membered cycloalkyl, 3-10 membered heterocyclyl, 6-10 membered aryl and 5-10 membered heteroaryl;
- or $X^1$, together with $L^1$, forms 3-10 membered cycloalkyl, 3-10 membered heterocyclyl or 5-6 membered monoheteroaryl; and/or $L^1$, together with some ring atoms of ring A, forms 3-10 membered cycloalkyl or 3-10 membered heterocyclyl; and/or $X^2$, together with some ring atoms of ring A, forms 3-10 membered cycloalkyl or 3-10 membered heterocyclyl; the 3-10 membered cycloalkyl, 3-10 membered heterocyclyl and 5-6 membered monoheteroaryl are optionally each independently substituted with a substituent selected from: $R^4$, $R^5$, $R^6$, halogen, amino, hydroxy, nitro, cyano, $C_{1-6}$ alkyl, $C_{1-6}$ alkoxy, $C_{1-6}$ alkylamino, di($C_{1-6}$ alkyl)amino, halo $C_{1-6}$ alkyl, hydroxy $C_{1-6}$ alkyl, amino $C_{1-6}$ alkyl and halo $C_{1-6}$ alkoxy; $R^a$ and $R^b$, when present, are each independently selected from hydrogen, $C_{1-6}$ alkyl, $C_{1-6}$ alkoxy, $C_{1-6}$ alkylamino, di($C_{1-6}$ alkyl)amino, halo $C_{1-6}$ alkyl, hydroxy $C_{1-6}$ alkyl, amino $C_{1-6}$ alkyl, halo $C_{1-6}$ alkoxy, 3-10 membered cycloalkyl, 3-10 membered heterocyclyl, 6-10 membered aryl and 5-10 membered heteroaryl; and m, n, p, q and t are each independently selected from 0, 1, 2, 3, 4 and 5.

In some embodiments, the present application provides a compound of the aforementioned general formula (I) or a pharmaceutically acceptable salt, ester or stereoisomer thereof, wherein:
- $M^1$, $M^2$, $M^3$, $M^4$, $M^5$, $M^6$ and $M^7$ are each independently selected from C, $C(R^1)$ and N, at least one of which is N;
- $X^1$, $X^2$, $X^3$ and $L^1$, when present, are each independently selected from —$C(R^5)(R^6)$—, —$N(R^4)$— and —O—;
- ring A is selected from 6-8 membered monoaryl and 5-8 membered monoheteroaryl;
- ring B is absent or selected from 3-8 membered cycloalkyl and 3-8 membered heterocyclyl;
- $R^1$, $R^2$, $R^3$, $R^5$ and $R^6$, when present, are each independently selected from hydrogen, halogen, nitro, cyano and the following groups optionally substituted with 1 to 3 $Q^1$: $C_{1-6}$ alkyl, —$OR^a$, —$NR^aR^b$, —$C(O)R^a$, —$C(O)OR^a$, —$OC(O)R^a$, —$OC(O)OR^a$, —$OC(O)NR^aR^b$, —$C(O)NR^aR^b$, —$NR^aC(O)R^b$, —$NR^aC(O)OR^b$, —$NR^aC(O)NR^aR^b$, 3-8 membered cycloalkyl, 3-8 membered heterocyclyl, 6-8 membered aryl and 5-8 membered heteroaryl; $Q^1$, when present, is independently selected from hydroxy, amino, halogen, nitro, cyano, $C_{1-6}$ alkyl, $C_{1-6}$ alkoxy, $C_{1-6}$ alkylamino, di($C_{1-6}$ alkyl)amino, halo $C_{1-6}$ alkyl, hydroxy $C_{1-6}$ alkyl, amino $C_{1-6}$ alkyl and halo $C_{1-6}$ alkoxy;
- $R^4$, when present, is independently selected from hydrogen and the following groups optionally substituted with 1 to 3 $Q^2$: $C_{1-6}$ alkyl, —$C(O)R^a$, —$C(O)OR^a$, —$C(O)NR^aR^b$, 3-8 membered cycloalkyl and 3-8 membered heterocyclyl; $Q^2$, when present, is independently selected from hydroxy, amino, halogen, nitro, cyano, $C_{1-6}$ alkyl, $C_{1-6}$ alkoxy, $C_{1-6}$ alkylamino, di($C_{1-6}$ alkyl)amino, halo $C_{1-6}$ alkyl, hydroxy $C_{1-6}$ alkyl, amino $C_{1-6}$ alkyl, halo $C_{1-6}$ alkoxy, 3-8 membered cycloalkyl and 3-8 membered heterocyclyl;
- or $X^1$, together with $L^1$, forms 3-8 membered cycloalkyl, 3-8 membered heterocyclyl or 5-6 membered monoheteroaryl; and/or $L^1$, together with some ring atoms of ring A, forms 3-8 membered cycloalkyl or 3-8 membered heterocyclyl; and/or $X^2$, together with some ring atoms of ring A, forms 3-8 membered cycloalkyl or 3-8 membered heterocyclyl; the 3-8 membered cycloalkyl, 3-8 membered heterocyclyl and 5-6 membered monoheteroaryl are optionally each independently substituted with a substituent selected from: $R^4$, $R^5$, $R^6$, halogen, amino, hydroxy, nitro, cyano, $C_{1-6}$ alkyl, $C_{1-6}$ alkoxy, $C_{1-6}$ alkylamino, di($C_{1-6}$ alkyl)amino, halo $C_{1-6}$ alkyl, hydroxy $C_{1-6}$ alkyl, amino $C_{1-6}$ alkyl and halo $C_{1-6}$ alkoxy;

$R^a$ and $R^b$, when present, are each independently selected from hydrogen, $C_{1-6}$ alkyl, $C_{1-6}$ alkoxy, $C_{1-6}$ alkylamino, di($C_{1-6}$ alkyl)amino, halo $C_{1-6}$ alkyl, hydroxy $C_{1-6}$ alkyl, amino $C_{1-6}$ alkyl, halo $C_{1-6}$ alkoxy, 3-8 membered cycloalkyl and 3-8 membered heterocyclyl; and m, n, p, q and t are each independently selected from 0, 1, 2, 3, 4 and 5.

In some embodiments, the present application provides a compound of the aforementioned general formula (I) or a pharmaceutically acceptable salt, ester or stereoisomer thereof, wherein:

$M^1$, $M^2$, $M^3$, $M^4$, $M^5$, $M^6$ and $M^7$ are each independently selected from C, C($R^1$) and N, at least one of which is N;

$X^1$ and $L^1$ are each independently selected from —C($R^5$)($R^6$)— and —N($R^4$)—;

$X^2$ and $X^3$, when present, are each independently selected from —C($R^5$)($R^6$)—, —N($R^4$)— and —O—;

ring A is selected from phenyl and 5-6 membered monoheteroaryl;

ring B is absent or selected from 3-6 membered monocycloalkyl and 3-6 membered monoheterocyclyl;

$R^1$, $R^2$, $R^3$, $R^5$ and $R^6$, when present, are each independently selected from hydrogen, halogen, nitro, cyano and the following groups optionally substituted with 1 to 3 $Q^1$: $C_{1-6}$ alkyl, —$OR^a$, —$NR^aR^b$, —$C(O)R^a$, —$C(O)OR^a$, —$C(O)NR^aR^b$, 3-6 membered cycloalkyl, 3-6 membered heterocyclyl, phenyl and 5-6 membered heteroaryl; $Q^1$, when present, is independently selected from hydroxy, amino, halogen, nitro, cyano, $C_{1-6}$ alkyl, $C_{1-6}$ alkoxy, $C_{1-6}$ alkylamino, di($C_{1-6}$ alkyl)amino, halo $C_{1-6}$ alkyl, hydroxy $C_{1-6}$ alkyl, amino $C_{1-6}$ alkyl and halo $C_{1-6}$ alkoxy;

$R^4$, when present, is independently selected from hydrogen and the following groups optionally substituted with 1 to 3 $Q^2$: $C_{1-6}$ alkyl, —$C(O)R^a$, 3-6 membered cycloalkyl and 3-6 membered heterocyclyl; $Q^2$, when present, is selected from hydroxy, amino, halogen, nitro, cyano, $C_{1-6}$ alkyl, $C_{1-6}$ alkoxy, $C_{1-6}$ alkylamino, di($C_{1-6}$ alkyl)amino, halo $C_{1-6}$ alkyl, hydroxy $C_{1-6}$ alkyl, amino $C_{1-6}$ alkyl, halo $C_{1-6}$ alkoxy, 3-6 membered cycloalkyl and 3-6 membered heterocyclyl;

or $X^1$, together with $L^1$, forms 3-6 membered monoheterocyclyl or 5-6 membered monoheteroaryl; and/or $L^1$, together with some ring atoms of ring A, forms 3-6 membered monocycloalkyl or 3-6 membered monoheterocyclyl; and/or $X^2$, together with some ring atoms of ring A, forms 3-6 membered monocycloalkyl and 3-6 membered monoheterocyclyl; the 3-6 membered monoheterocyclyl, 5-6 membered monoheteroaryl and 3-6 membered monocycloalkyl are optionally each independently substituted with a substituent selected from: $R^4$, $R^5$, $R^6$, halogen, amino, hydroxy, $C_{1-6}$ alkyl, $C_{1-6}$ alkoxy, $C_{1-6}$ alkylamino, di($C_{1-6}$ alkyl)amino, halo $C_{1-6}$ alkyl, hydroxy $C_{1-6}$ alkyl, amino $C_{1-6}$ alkyl and halo $C_{1-6}$ alkoxy;

$R^a$ and $R^b$, when present, are each independently selected from hydrogen, $C_{1-6}$ alkyl, $C_{1-6}$ alkoxy, $C_{1-6}$ alkylamino, di($C_{1-6}$ alkyl)amino, halo $C_{1-6}$ alkyl, hydroxy $C_{1-6}$ alkyl, amino $C_{1-6}$ alkyl, halo $C_{1-6}$ alkoxy, 3-6 membered cycloalkyl and 3-6 membered heterocyclyl;

m is 1, 2 or 3;

n, p and q are each independently selected from 0, 1, 2 and 3; and t is 0 or 1.

In some embodiments, the present application provides a compound of the aforementioned general formula (I) or a pharmaceutically acceptable salt, ester or stereoisomer thereof, wherein the compound is of the structure shown as general formula (II),

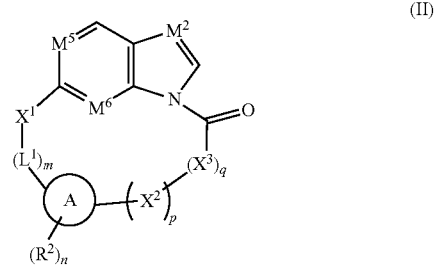

(II)

wherein:

$M^2$, $M^5$ and $M^6$ are each independently selected from CH and N; and $X^1$, $X^2$, $X^3$, $L^1$, A, $R^2$, m, n, p and q are described as above for general formula (I).

In some embodiments, the present application provides a compound of the aforementioned general formula (I) or a pharmaceutically acceptable salt, ester or stereoisomer thereof, wherein the compound is of the structure shown as general formula (III),

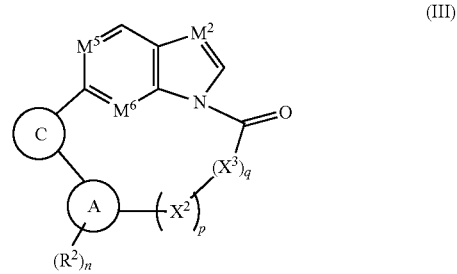

(III)

wherein:

ring C is selected from 3-6 membered saturated monoheterocyclyl and 5-6 membered nitrogen-containing monoheteroaryl, preferably 5-6 membered saturated monoheterocyclyl; the 3-6 membered saturated monoheterocyclyl and 5-6 membered nitrogen-containing monoheteroaryl are optionally each independently substituted with a substituent selected from: $R^4$, R, $R^6$, halogen, amino, hydroxy, $C_{1-4}$ alkyl, $C_{1-4}$ alkoxy, $C_{1-4}$ alkylamino, di($C_{1-4}$ alkyl)amino, halo $C_{1-4}$ alkyl, hydroxy $C_{1-4}$ alkyl, amino $C_{1-4}$ alkyl and halo $C_{1-4}$ alkoxy;

—$(X^2)_p$— is selected from —$C(R^5)(R^6)$—, —$C(R^5)(R^6)$—$C(R^5)(R^6)$—, —$N(R^4)$—$C(R^5)(R^6)$—, —O—$C(R^5)(R^6)$—, —$C(R^5)(R^6)$—$N(R^4)$— and —$C(R^5)(R^6)$—O—, and the left chemical bond thereof is connected to ring A and the right chemical bond thereof is connected to $X^3$;

—$(X^3)_q$— is selected from —$C(R^5)(R^6)$—, —$C(R^5)(R^6)$—$C(R^5)(R^6)$—, —$N(R^4)$—$C(R^5)(R^6)$—, —O—$C(R^5)(R^6)$—, —$C(R^5)(R^6)$—$N(R^4)$— and —$C(R^5)(R^6)$—O—, and the left chemical bond thereof is connected to $X^2$ and the right chemical bond thereof is connected to carbonyl;

ring A is selected from phenyl and 5-6 membered monoheteroaryl, preferably 5-6 membered nitrogen-containing heteroaryl;

$R^2$, when present, is independently selected from hydrogen, halogen and the following groups optionally substituted with 1 to 3 $Q^1$: $C_{1-4}$ alkyl, —$OR^a$ and —$NR^aR^b$; $Q^1$, when present, is independently selected from hydroxy, amino, halogen, nitro, cyano, $C_{1-4}$ alkyl, $C_{1-4}$ alkoxy, $C_{1-4}$ alkylamino, di($C_{1-4}$ alkyl)amino, halo $C_{1-4}$ alkyl, hydroxy $C_{1-4}$ alkyl, amino $C_{1-4}$ alkyl and halo $C_{1-4}$ alkoxy;

$R^a$ and $R^b$, when present, are each independently selected from hydrogen and $C_{1-4}$ alkyl;

$R^5$ and $R^6$, when present, are each independently selected from hydrogen, halogen, hydroxy, amino, $C_{1-4}$ alkyl and $C_{1-4}$ alkoxy;

$R^4$, when present, is independently selected from hydrogen and $C_{1-4}$ alkyl optionally substituted with 1 to 2 $Q^2$; $Q^2$, when present, is independently selected from hydroxy, amino, halogen and $C_{1-4}$ alkoxy;

n is 0, 1 or 2; and $M^1$, $M^5$ and $M^6$ are described as above for general formula (I) or (II).

In some embodiments, the present application provides a compound of the aforementioned general formula (III) or a pharmaceutically acceptable salt, ester or stereoisomer thereof, wherein ring C is optionally substituted 5-6 membered saturated monoheterocyclyl, more preferably optionally substituted 5-6 saturated nitrogen-containing heterocyclyl.

In some embodiments, the present application provides a compound of the aforementioned general formula (III) or a pharmaceutically acceptable salt, ester or stereoisomer thereof, wherein the compound is of the structure shown as general formula (IV),

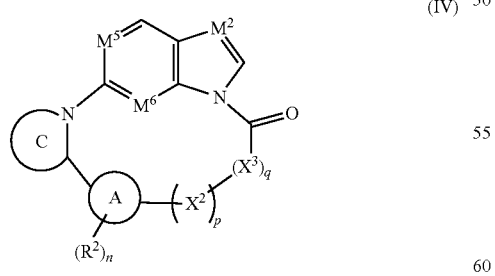

(IV)

wherein each optional substituent on ring C is independently selected from $R^4$, $R^5$, $R^6$, halogen, amino, hydroxy, nitro, cyano, $C_{1-6}$ alkyl, $C_{1-6}$ alkoxy, $C_{1-6}$ alkylamino, di($C_{1-6}$ alkyl)amino, halo $C_{1-6}$ alkyl, hydroxy $C_{1-6}$ alkyl, amino $C_1$, alkyl and halo $C_1$, alkoxy.

In some embodiments, the present application provides a compound of the aforementioned general formula (III) or a pharmaceutically acceptable salt, ester or stereoisomer thereof, wherein:

ring C is selected from aziridinyl, azetidinyl, pyrrolidinyl, imidazolidinyl, pyrazolidinyl, piperidinyl, morpholinyl, piperazinyl, hexahydropyridazinyl, hexahydropyrimidinyl, pyrrolyl, imidazolyl, pyrazolyl, pyridinyl or pyrimidinyl; each of which is optionally substituted with a substituents selected from: fluorine, chlorine, bromine, iodine, hydroxy, amino, methyl, ethyl, propyl, isopropyl, butyl, isobutyl, sec-butyl, methoxy, ethoxy, propoxy, isopropoxy, methylamino, dimethylamino, ethylamino, diethylamino, trifluoromethyl and trifluoromethoxy;

ring A is selected from phenyl, pyrrolyl, imidazolyl, pyrazolyl, thiazolyl, oxazolyl, isoxazolyl, thiazolyl, isothiazolyl, 1,2,4-triazolyl, 1,2,3-triazolyl, 1,3,4-oxadiazolyl, 1,2,4-oxadiazolyl, 1,3,4-thiadiazolyl, 1,2,4-thiadiazolyl, pyridinyl, pyrimidinyl, pyridazinyl, 1,3,5-triazinyl and tetrazinyl;

$R^2$, when present, is independently selected from hydrogen, fluorine, chlorine, bromine, iodine, hydroxy, amino, methyl, ethyl, propyl, isopropyl, butyl, isobutyl, sec-butyl, methylamino, dimethylamino, ethylamino, diethylamino, methoxy, ethoxy, propoxy, isopropoxy, trifluoromethyl and trifluoromethoxy;

$R^5$ and $R^6$, when present, are each independently selected from hydrogen, fluorine, chlorine, bromine, iodine, hydroxy, amino, methyl, ethyl, propyl, isopropyl, butyl, isobutyl, sec-butyl, methoxy, ethoxy, propoxy and isopropoxy; and $R^4$, when present, is independently selected from hydrogen, methyl, ethyl, propyl, isopropyl, butyl, isobutyl and sec-butyl.

In some embodiments, the present application provides a compound of the aforementioned general formulas (I)—(IV) or a pharmaceutically acceptable salt, ester or stereoisomer thereof, wherein:

ring A is selected from

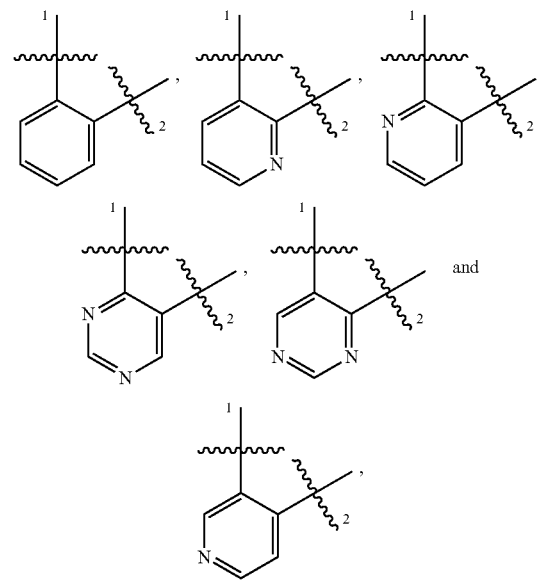

and preferably the wavy line marked with "1" represents the connection point of ring A to LV and the wavy line marked with "2" represents the connection point of ring A to $X^2$;

—$(X^2)_p$— is selected from —$C(R^5)(R^6)$—, —$C(R^5)(R^6)$—$C(R^5)(R^6)$—, —$N(R^4)$—$C(R^5)(R^6)$— and —O—$C(R^5)(R^6)$—, and preferably the left chemical bond thereof is connected to ring A and the right chemical bond thereof is connected to $X^3$; and —$(X^3)_q$— is selected from —$C(R^5)(R^6)$—, —$C(R^5)(R^6)$—$N(R^4)$— and —$C(R^5)(R^6)$—O—, and preferably the left chemical bond thereof is connected to $X^2$ and the right chemical bond thereof is connected to carbonyl.

In some embodiments, the present application provides a compound of the aforementioned general formula (I) or a pharmaceutically acceptable salt, ester or stereoisomer thereof, wherein the compound is of the structure shown as general formula (V),

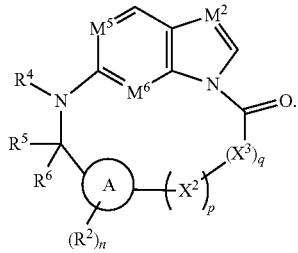

(V)

In some embodiments, the present application provides a compound of the aforementioned general formula (I) or a pharmaceutically acceptable salt, ester or stereoisomer thereof, wherein:

$X^1$ is —$N(R^4)$—;
$L^1$ is —$C(R^5)(R^6)$—;
ring A is selected from phenyl and 5-6 membered nitrogen-containing heteroaryl;
$R^2$, when present, is independently selected from hydrogen, halogen and the following groups optionally substituted with 1 to 3 $Q^1$: $C_{1-4}$ alkyl, —$OR^a$ and —$NR^aR^b$; $Q^1$, when present, is independently selected from hydroxy, amino, halogen, nitro, cyano, $C_{1-4}$ alkyl, $C_{1-4}$ alkoxy, $C_{1-4}$ alkylamino, di($C_{1-4}$ alkyl)amino, halo $C_{1-4}$ alkyl, hydroxy $C_{1-4}$ alkyl, amino $C_{1-4}$ alkyl and halo $C_{1-4}$ alkoxy;
$R^a$ and $R^b$, when present, are each independently selected from hydrogen and $C_{1-4}$ alkyl;
$R^5$ and $R^6$, when present, are each independently selected from hydrogen, halogen, hydroxy, amino, $C_{1-4}$ alkyl and $C_{1-4}$ alkoxy;
$R^4$, when present, is independently selected from hydrogen and $C_{1-4}$ alkyl optionally substituted with 1 to 2 $Q^2$;
$Q^2$, when present, is independently selected from hydroxy, amino, halogen and $C_{1-4}$ alkoxy; and
n is 0, 1 or 2.

In some embodiments, the present application provides a compound of the aforementioned general formula (I) or a pharmaceutically acceptable salt, ester or stereoisomer thereof, wherein:

ring A is selected from phenyl, pyrrolyl, imidazolyl, pyrazolyl, furyl, thienyl, thiazolyl, oxazolyl, isoxazolyl, thiazolyl, isothiazolyl, 1,2,4-triazolyl, 1,2,3-triazolyl, 1,3,4-oxadiazolyl, 1,2,4-oxadiazolyl, 1,3,4-thiadiazolyl, 1,2,4-thiadiazolyl, pyridinyl, pyrimidinyl, pyridazinyl, 1,3,5-triazinyl and tetrazinyl;

$R^2$, when present, is independently selected from hydrogen, fluorine, chlorine, bromine, iodine, hydroxy, amino, methyl, ethyl, propyl, isopropyl, butyl, isobutyl, sec-butyl, methylamino, dimethylamino, ethylamino, diethylamino, methoxy, ethoxy, propoxy, isopropoxy, trifluoromethyl and trifluoromethoxy;

$R^5$ and $R^6$, when present, are each independently selected from hydrogen, fluorine, chlorine, bromine, iodine, hydroxy, amino, methyl, ethyl, propyl, isopropyl, butyl, isobutyl, sec-butyl, methoxy, ethoxy, propoxy and isopropoxy; and $R^4$, when present, is independently selected from hydrogen, methyl, ethyl, propyl, isopropyl, butyl, isobutyl and sec-butyl.

In some embodiments, the present application provides a compound of the aforementioned general formula (I) or a pharmaceutically acceptable salt, ester or stereoisomer thereof, wherein:

ring A is selected from

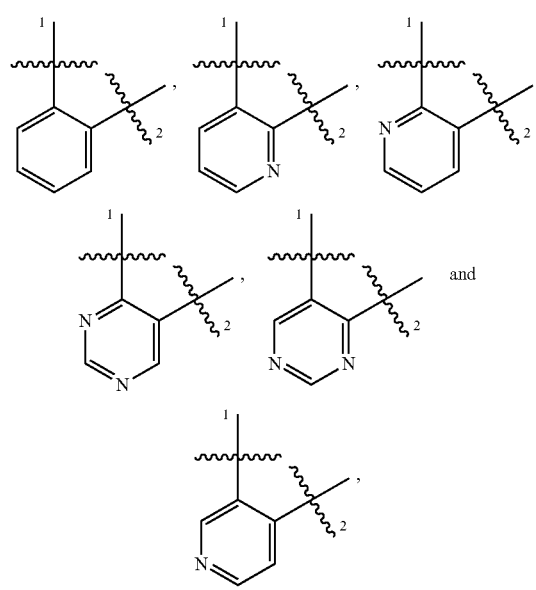

and preferably the wavy line marked with "1" represents the connection point of ring A to $L^1$ and the wavy line marked with "2" represents the connection point of ring A to $X^2$;

—$(X^2)_p$— is selected from —$C(R^5)(R^6)$—, —$C(R^5)(R^6)$—$C(R^5)(R^6)$—, —$N(R^4)$—$C(R^5)(R^6)$— and —O—$C(R^5)(R^6)$—, and preferably the left chemical bond thereof is connected to ring A and the right chemical bond thereof is connected to $X^3$; and —$(X^3)_q$— is selected from —$C(R^5)(R^6)$—, —$C(R^5)(R^6)$—$N(R^4)$— and —$C(R^5)(R^6)$—O—, and preferably the left chemical bond thereof is connected to $X^2$ and the right chemical bond thereof is connected to carbonyl.

Any substituent and any optional group thereof in the aforementioned technical solution described in the present application can be combined with each other to form a new and complete technical solution, and the formed new technical solution is encompassed within the scope of the present invention.

In some embodiments, the present application provides a compound of the aforementioned general formula (I) or a pharmaceutically acceptable salt, ester or stereoisomer thereof, wherein the compound is selected from:

| No. | Compound |
|---|---|
| Compound 1 | |
| Compound 2 | |
| Compound 2-1 | |
| Compound 3 | |
| Compound 3-1 | |
| Compound 4 | |
| Compound 5 | |
| Compound 6 | |
| Compound 7 | |
| Compound 8 | |
| Compound 9 | |

| No. | Compound |
|---|---|
| Compound 10 | |
| Compound 11 | |
| Compound 11-1 | |
| Compound 12 | |
| Compound 13 | |
| Compound 13-1 | |
| Compound 14 | |
| Compound 15 | |
| Compound 16 | |
| Compound 17 | |

\* represents that the carbon atom is a chiral carbon atom having a single configuration (R configuration or S configuration).

In some embodiments, the present application provides a compound of the aforementioned general formula (I) or a pharmaceutically acceptable salt, ester or stereoisomer thereof, wherein the compound is selected from:

| No. | Compound |
|---|---|
| Compound 2' | 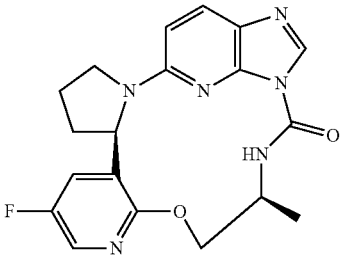 [SMILES: C[C@H]1COc2ncc(F)cc2[C@H]2CCCN2c2ccc3ncn(c3n2)C(=O)N1] |
| Compound 3' | 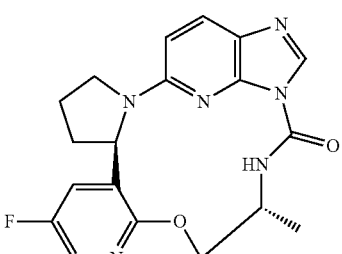 |
| Compound 11' | 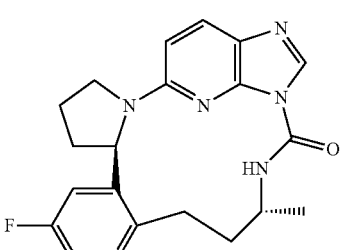 |

In another aspect, the present application provides a pharmaceutical formulation comprising a compound of the aforementioned general formula (I), (II), (III), (IV) or (V), or a pharmaceutically acceptable salt, ester or stereoisomer thereof, and one or more pharmaceutically acceptable carriers and/or excipients. The pharmaceutical formulation may be any pharmaceutically acceptable dosage form. Pharmaceutically acceptable excipients are substances that are non-toxic, compatible with active ingredient, and otherwise biologically compatible with organism. The choice of a particular excipient will depend on an administration mode used to treat a particular patient or disease type and state. Examples of pharmaceutically acceptable excipient include, but are not limited to, solvents, diluents, dispersant, suspending agents, surfactants, isotonizing agent, thickening agents, emulsifiers, binders, lubricants, stabilizers, hydrating agents, emulsification accelerators, buffers, absorbents, colorants, ion exchangers, mold release agents, coating agents, flavoring agents, antioxidants and the like which are conventional in the pharmaceutical field. If necessary, perfuming agents, preservatives, sweeteners and the like may be further added to the pharmaceutical composition.

In some embodiments, the above pharmaceutical formulations may be administered to a patient or subject in need of such treatment via oral, parenteral, rectal, or pulmonary administration and the like. For oral administration, the pharmaceutical composition may be prepared into oral formulations, for example conventional oral solid formulations such as tablets, capsules, pills, granules and the like; or can also be prepared into oral liquid formulations such as oral solutions, oral suspensions, syrups and the like. When the pharmaceutical compositions are prepared into oral formulations, suitable fillers, binders, disintegrants, lubricants and the like may be added. For parenteral administration, the above pharmaceutical formulations may also be prepared into injection formulations, including injections, sterile powders for injection and concentrated solutions for injection. The injection formulations can be prepared by a conventional method known in the pharmaceutical field, and during the preparation, no additive may be added, or suitable additives may be added according to the properties of the drug. For rectal administration, the pharmaceutical compositions may be prepared into suppositories and the like. For pulmonary administration, the pharmaceutical compositions may be prepared into inhalation formulations, aerosols, powder spray or spray and the like.

In another aspect, the present application also provides a pharmaceutical composition comprising a compound of the aforementioned general formula (I), (II), (III), (IV) or (V), or a pharmaceutically acceptable salt, ester or stereoisomer thereof, and one or more second therapeutically active agents for use in combination with the tyrosine kinase inhibitor compounds of the present application in the treatment and/or prevention of tyrosine kinase-mediated diseases and related conditions, such as pain, cancer, inflammation, neurodegenerative diseases, autoimmune diseases, infectious diseases and the like.

The pain may be of any origin or etiology, including but not limited to one or more of inflammatory pain, visceral pain, cancer-induced pain, chemotherapy pain, wound pain, surgical and postoperative pain, labor pain, acute pain, chronic pain, intractable pain, somatic pain, nociceptive pain, neuropathic pain, blood-borne pain, immunogenetric pain, endocrine-derived pain, metabolic-induced pain, cardiogenic pain, headache, phantom limb pain and dental pain. Therapeutically active agents suitable for use in combination therapy for pain include, but are not limited to, Nav1.7 channel modulators, opioid analgesics, non-steroidal anti-inflammatory drugs, sedatives, selective/non-selective cyclooxygenase inhibitors, antiepileptics, antidepressants, local anesthetics, 5-HT receptor blockers, 5-HT receptor agonists, ergot alkaloids, β-receptor blockers, M receptor blockers, nitrates, vitamin K and the like.

The cancer includes, but is not limited to, one or more of lung cancer, colon cancer, prostate cancer, breast cancer, liver cancer, lymphoma, thyroid cancer, multiple myeloma, soft tissue sarcoma, ovarian cancer, cervical cancer, fallopian tube carcinoma, renal cell carcinoma, gastric cancer, gastrointestinal stromal tumor, bone cancer, basal cell carcinoma, peritoneal cancer, dermatofibroma, pancreatic cancer, esophageal cancer, glioblastoma, head and neck cancer, inflammatory myofibroblast tumor and anaplastic large cell lymphoma. Second therapeutically active agents suitable for use in combination therapy for cancer include, but are not limited to, mitotic inhibitors, alkylating agents, antimetabolites, antisense DNA or RNA, antitumor antibiotics, growth factor inhibitors, signal transduction inhibitors, cell cycle inhibitors, enzyme inhibitors, retinoid receptor modulators, proteasome inhibitors, topoisomerase inhibitors, biological response modifiers, hormones, angiogenesis inhibitors, cell growth inhibitors, targeted antibodies, HMG-CoA reductase inhibitors, prenyl-protein transferase inhibitors and the like.

The inflammation includes, but is not limited to, atherosclerosis, allergy, and inflammation due to infection or injury. Therapeutically active agents suitable for use in combination therapy for inflammation include, but are not limited to, steroidal anti-inflammatory drugs and non-steroidal anti-inflammatory drugs.

The neurodegenerative disease includes, but is not limited to, one or more of Alzheimer's disease, Parkinson's disease, amyotrophic lateral sclerosis and Huntington's disease. Therapeutically active agents suitable for use in the combination therapy for neurodegenerative diseases include, but are not limited to, dopamine-mimetics, dopamine receptor agonists, agents affecting dopamine metabolism, NMDA receptor antagonists, adenosine $A_{2A}$ receptor inhibitors, agents affecting DA release and reuptake, central anticholinergics, cholinesterase inhibitors, 5-HT agonists, α2 adrenergic receptor antagonists, antidepressants, cholinergic receptor agonists, β/γ secretase inhibitors, H3 receptor antagonists or antioxidant agents and the like.

The autoimmune disease includes, but is not limited to, one or more of rheumatoid arthritis, Sjogren's syndrome, type I diabetes and lupus erythematosus. Therapeutically active agents suitable for use in the combination therapy for autoimmune diseases include, but are not limited to, anti-rheumatic drugs, non-steroidal anti-inflammatory drugs, glucocorticoid drugs, TNF antagonists, cyclophosphamide, mycophenolate mofetil, cyclosporine and the like, which is used for alleviating the disease.

The infectious diseases include trypanosomiasis and the like.

In some embodiments, the pharmaceutical compositions further comprise one or more pharmaceutically acceptable excipients described as above.

In some embodiments, the compound of general formula (I), (II), (III), (IV) or (V), or the pharmaceutically acceptable salt, ester or stereoisomer thereof, and the second therapeutically active agent may be present in one formulation, i.e., as a combined formulation, or may be present in separate formulations simultaneously or sequentially administrating to a subject.

In another aspect, the present application also relates to uses of the compound of the aforementioned general formula (I), (II), (III), (IV) or (V), or the pharmaceutically acceptable salt, ester or stereoisomer thereof in the preparation of medications for the treatment and/or prevention of diseases and related conditions mediated by one or more tyrosine kinases of TRK, ALK and/or ROS1.

In some embodiments, the diseases and related conditions mediated by one or more tyrosine kinases of TRK, ALK and/or ROS1 include, but are not limited to, pain, cancer, inflammation, neurodegenerative disease, autoimmune disease, infectious disease and the like. The cancer includes, but is not limited to, lung cancer, colon cancer, rectal cancer, prostate cancer, breast cancer, liver cancer, gallbladder cancer, cholangiocarcinoma, leukemia, melanoma, lymphoma, thyroid cancer, multiple myeloma, soft tissue sarcoma, ovarian cancer, cervical cancer, fallopian tube carcinoma, renal cell carcinoma, gastric cancer, gastrointestinal stromal tumor, bone cancer, basal cell carcinoma, peritoneal cancer, dermatofibroma, pancreatic cancer, esophageal cancer, glioblastoma, head and neck cancer, inflammatory myofibroblast tumor, anaplastic large cell lymphoma or neuroblastoma and the like. The pain, inflammation, neurodegenerative disease, autoimmune disease and infectious disease are defined as above.

In some embodiments, the lung cancer includes small cell lung cancer and non-small cell lung cancer. In some embodiments, the non-small cell lung cancer comprises lung adenocarcinoma, squamous cell carcinoma and large cell carcinoma.

In some embodiments, the cancers mediated by one or more tyrosine kinases of TRK, ALK and/or ROS1 include a cancer that is at least partially resistant to one or more existing target therapeutically active agents.

In some embodiments, the cancer resistance is caused by one or more mutations in the gene encoding TRK, ALK and/or ROS1 kinase receptors.

In some embodiments, the mutation sites of the ALK target are located at L1196M, L1152R, G1202R, G1269A, G1269S, 1151Tins, S1206R, S1206Y/C, C1156Y, F1174L, F1174S, R1050H, F1245C/I/L/V, R1275L/Q, T1151M, M1166R, I1170N, I1170S, I1171N, I1171T, I1171S, V1180L, I1183T, L1196M, A1200V, L1204F, L1240V, D1270G, Y1278S, R1192P, G1128A, G1286R, T1343I, D1203N, E1210K, F1174S, F1174C/L/V, F1245C/L, L1252R, G1296M/Q, T1151K/M, V1180L and the like in polypeptide. In some embodiments, the mutation sites of the ROS1 target are located at G2032R, D2033N, S1986F, L2026M, L1951R, L2155S, G2101A, K2003I and the like in polypeptide. In some embodiments, the mutation sites of the TRK target are located at G517R, A542V, V573M, F589L, F589C, G595R, G595S, D596V, F600L, F646V, C656Y, C656F, L657V, G667S, G667C, Y676S, G623R, G667C, G623E, L686M, G545R, A570V, Q596E, Q596P, V601G, F617L, F617C, G623S, D624V, R630K, C682Y, C682F, L683V, G693S, G713S, C685F, C685Y, L686V, G696A, G639R and the like in polypeptide.

In some embodiments, the compound of the present application may also be used to treat diseases and related conditions mediated by tyrosine kinases selected from JAK2, SRC, FYN, LYN, YES, FGR, FAK, ARK5 or any combination thereof, preferably the diseases are cancers.

In another aspect, the present application also provides a method for treating diseases and related conditions mediated by one or more tyrosine kinases of TRK, ALK and ROS1, comprising administering to a patient in need thereof an effective amount of compound of the aforementioned general formula (I), (II), (III), (IV) or (V) or the pharmaceutically acceptable salt, ester or stereoisomer thereof, the aforementioned pharmaceutical formulation, or the aforementioned pharmaceutical composition, wherein the diseases and related conditions mediated by one or more tyrosine kinases of TRK, ALK and ROS1 are described as above.

The "effective amount" refers to a dosage of a drug that is capable of reducing, delaying, inhibiting or curing the condition in a subject. The amount of the administered dose is determined by factors such as the administration mode of drugs, the pharmacokinetics of agents, the severity of diseases, and the individual signs (sex, weight, height, age) of the subject.

In another aspect, the present application also provides a method for preparing a compound of general formula (I), comprising the steps as follows:

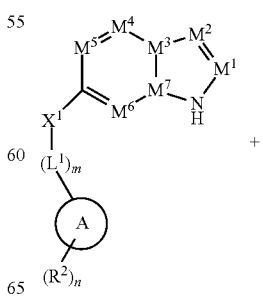

Intermediate 1

-continued

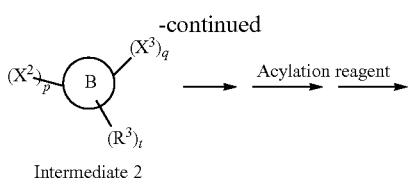

Intermediate 2

$$\text{General formula (I)}$$

intermediate 1 and intermediate 2 are subjected to a plurality of reactions such as substitution reaction, deprotection reaction, acylation reaction (using an acylation reagent) and the like in the presence of an organic solvent and a catalyst at a proper temperature to obtain the compound of the general formula (I).

The substituents and variables in the above formulas are defined as above.

The organic solvent includes a common reaction solvent known to those skilled in the art, which may be a polar solvent or a non-polar solvent, a protic solvent or a non-protic solvent, and preferably a polar non-protic solvent such as dichloromethane, trichloromethane, tetrahydrofuran, acetonitrile, dimethylformamide, dimethyl sulfoxide and the like.

The catalyst includes a dehydration catalyst and a base catalyst. Examples of the dehydration catalyst include diethyl azodicarboxylate, azobisformyl dipiperidine, tributylphosphine and the like. The base catalyst includes an organic base and an inorganic base, preferably an organic base, more preferably an organic amine bases such as triethylamine, pyridine, N,N-diisopropylethylamine and the like.

Examples of the substitution reaction include the reaction between acids and alcohols to make esters, dehydration between alcohols to make ethers, and dehydration between carboxylic acids to make acid anhydrides.

The deprotection reaction may be, for example, a reaction for removing hydroxy or amino protecting groups.

The acylation reaction may be, for example, a reaction between acylation agents and amino or hydroxy to make amides or esters.

The intermediates involved in the preparation method of the present application are either commercially available or self-made, and can be prepared by those skilled in the art according to known conventional chemical reactions, and the preparation method thereof is also within the scope of the present application.

In the present application, all compounds are named according to chemical structures thereof, and if a compound name is not consistent with chemical structure thereof for the same compound, the chemical structure shall prevail.

In the present application, unless otherwise specified, scientific and technical terms used herein have the meanings generally understood by those skilled in the art, however, in order to better understand the present invention, definitions of some terms are provided below. If the definitions of terms provided herein are not consistent with the meanings generally understood by those skilled in the art, the definitions and explanations of the terms provided in the present application shall prevail.

The "halogen" described herein refers to fluorine, chlorine, bromine or iodine.

The "$C_{1-6}$ alkyl" described herein refers to a straight-chain or branched alkyl having 1 to 6 carbon atoms, and includes, for example, "$C_{1-5}$ alkyl", "$C_{1-4}$ alkyl", "$C_{1-3}$ alkyl", "$C_{1-2}$ alkyl", "$C_{2-6}$ alkyl", "$C_{2-5}$ alkyl", "$C_{2-4}$ alkyl", "$C_{2-3}$ alkyl", "$C_{3-6}$ alkyl", "$C_{3-5}$ alkyl", "$C_{3-4}$ alkyl", "$C_{4-6}$ alkyl", "$C_{4-5}$ alkyl", "$C_{5-6}$ alkyl" and the like. Examples of $C_{1-6}$ alkyl include, but are not limited to, methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl and the like. The "$C_{1-4}$ alkyl" described herein refers to a specific example having 1 to 4 carbon atoms in the $C_{1-6}$ alkyl.

The "$C_{1-6}$ alkoxy" described herein refers to "$C_{1-6}$ alkyl-O—", wherein "$C_{1-6}$ alkyl" is defined as above. The "$C_{1-4}$ alkoxy" described herein refers to "$C_{1-4}$ alkyl-O—", wherein "$C_{1-4}$ alkyl" is defined as above.

The "$C_{2-6}$ alkenyl" described herein refers to a straight-chain, branched or cyclic alkenyl having at least one double bond and 2 to 6 carbon atoms, and includes, for example, "$C_{2-5}$ alkenyl", "$C_{2-4}$ alkenyl", "$C_{2-3}$ alkenyl", "$C_{3-6}$ alkenyl", "$C_{3-5}$ alkenyl", "$C_{3-4}$ alkenyl", "$C_{4-6}$ alkenyl", "$C_{4-5}$ alkenyl", "$C_{5-6}$ alkenyl" and the like. Examples of $C_{2-6}$ alkenyl include, but are not limited to, ethenyl, 1-propenyl, 2-propenyl, 1-butenyl, 2-butenyl, 1,3-butadienyl, 1-pentenyl, 2-pentenyl, 3-pentenyl, 1,3-pentadienyl, 1,4-pentadienyl, 1-hexenyl, 2-hexenyl, 3-hexenyl, 1,4-hexadienyl, cyclopentenyl, 1,3-cyclopentadienyl, cyclohexenyl, 1,4-cyclohexadienyl and the like.

The "hydroxy $C_{1-6}$ alkyl", "amino $C_{1-6}$ alkyl" and "halo $C_{1-6}$ alkyl" described herein each refer to the group wherein the hydrogen of $C_{1-6}$ alkyl group is substituted by one or more hydroxy, amino or halogen groups, and wherein the $C_{1-6}$ alkyl is defined as above.

The "halo $C_{1-6}$ alkoxy" described herein refers to $C_{1-6}$ alkoxy group wherein the hydrogen is substituted by one or more halogen groups.

The "$C_{1-6}$ alkylamino" and "di($C_{1-6}$ alkyl)amino" described herein refer to $C_{1-6}$ alkyl-NH— and

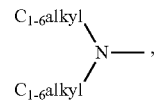

respectively.

The "ring B is absent" described herein refers to $X^2$ directly connected with $X^3$ by a single chemical bond.

The "3-10 membered cycloalkyl" includes "3-8 membered cycloalkyl" and "8-10 membered fused cycloalkyl".

The "3-8 membered cycloalkyl" described herein refers to a saturated or partially saturated and non-aromatic monocyclic cycloalkyl having 3 to 8 ring carbon atoms, and includes "3-8 membered saturated cycloalkyl" and "3-8 membered partially saturated cycloalkyl", and preferably "3-4 membered cycloalkyl", "3-5 membered cycloalkyl", "3-6 membered cycloalkyl", "3-7 membered cycloalkyl", "4-5 membered cycloalkyl", "4-6 membered cycloalkyl", "4-7 membered cycloalkyl", "4-8 membered cycloalkyl", "5-6 membered cycloalkyl", "5-7 membered cycloalkyl", "5-8 membered cycloalkyl", "6-7 membered cycloalkyl", "6-8 membered cycloalkyl", "7-8 membered cycloalkyl", "3-6 membered saturated cycloalkyl", "5-8 membered saturated cycloalkyl", "5-7 membered saturated cycloalkyl", "5-6 membered saturated cycloalkyl" and the like. Specific examples of "3-8 membered saturated cycloalkyl" include, but are not limited to, cyclopropyl, cyclobutyl, cyclopentyl, cyclohexyl, cycloheptyl, cyclooctyl and the like; specific examples of the "3-8 membered partially saturated cycloalkyl" include, but are not limited to, cyclopropenyl, cyclobutenyl, cyclopentenyl, cyclopentadienyl, cyclohexenyl, cyclohex-1,3-dienyl, cyclohex-1,4-dienyl, cycloheptenyl, cyclohept-1,3-dienyl, cyclohept-1,4-dienyl, cyclohept-1,3,5-trienyl, cyclooctenyl, cyclooct-1,3-dienyl, cyclooct-1,4-dienyl, cyclooct-1,5-dienyl, cyclooct-1,3,5-trienyl, cyclooctatetraenyl and the like.

The "8-10 membered fused cycloalkyl" described herein refers to a saturated or partially saturated and non-aromatic cycloalkyl having 8 to 10 ring carbon atoms, which is formed by two or more cyclic structures sharing two adjacent carbon atoms (one ring of the fused cycloalkyl may be an aromatic ring, but the fused cycloalkyl as a whole is non-aromatic), and includes "8-9 membered fused cycloalkyl", "9-10 membered fused cycloalkyl" and the like, which may be fused in a manner as 5-6 membered cycloalkano 5-6 membered cycloalkyl, benzo 5-6 membered cycloalkyl and the like. Examples of 8-10 membered fused cycloalkyl include, but are not limited to, bicyclo[3.1.0]hexyl, bicyclo[4.1.0]heptyl, bicyclo[2.2.0]hexyl, bicyclo[3.2.0]heptyl, bicyclo[4.2.0]octyl, octahydro cyclopentadienyl, octahydro-1H-indenyl, decahydronaphthyl, tetradecahydrophenanthryl, bicyclo[3.1.0]hex-2-enyl, bicyclo[4.1.0]hept-3-enyl, bicyclo[3.2.0]hept-3-enyl, bicyclo[4.2.0]oct-3-enyl, 1,2,3,3a-tetrahydrocyclopentadienyl, 2,3,3a,4,7,7a-hexahydro-1H-indenyl, 1,2,3,4,4a,5,6,8a-octahydronaphthyl, 1,2,4a,5,6,8a-hexahydronaphthyl, 1,2,3,4,5,6,7,8,9,10-decahydrophenanthryl, benzocyclopentyl, benzocyclohexyl, benzocyclohexenyl, benzocyclopentenyl and the like.

The "3-10 membered heterocyclyl" described herein includes "3-8 membered heterocyclyl" and "8-10 membered fused heterocyclyl".

The "3-8 membered heterocyclyl" described herein refers to a saturated or partially saturated and non-aramatic monocyclic cyclic group having 3 to 8 ring atoms, which contains at least one (e.g., 1, 2, 3, 4 or 5) ring heteroatom(s), and the heteroatoms are nitrogen atoms, oxygen atoms and/or sulfur atoms. Optionally, a ring atom (e.g., a carbon atom, a nitrogen atom, or a sulfur atom) may be substituted by an oxo group (forming, for example, a C=O, N=O, S=O or SO$_2$ ring member). The "3-8 membered heterocyclyl" includes "3-8 membered saturated heterocyclyl" and "3-8 membered partially saturated heterocyclyl". Preferably, the "3-8 membered heterocyclyl" contains 1 to 3 heteroatoms such as one or two heteroatoms selected from nitrogen and oxygen atoms, or one nitrogen atom. Preferably, the "3-8 membered heterocyclyl" is "3-7 membered heterocyclyl", "3-6 membered heterocyclyl", "4-7 membered heterocyclyl", "4-6 membered heterocyclyl", "6-8 membered heterocyclyl", "5-7 membered heterocyclyl", "5-6 membered heterocyclyl", "3-6 membered saturated heterocyclyl", "3-6 membered nitrogen-containing heterocyclyl", "3-6 membered saturated nitrogen-containing heterocyclyl", "5-6 membered nitrogen-containing heterocyclyl", "5-6 membered saturated nitrogen-containing heterocyclyl" and the like. The "3-8 membered heterocyclyl" may, for example, contains only one or two nitrogen atoms, or contains one nitrogen atom and one or two other heteroatoms (e.g., oxygen atoms and/or sulfur atoms). Specific examples of "3-8 membered heterocyclyl" include, but are not limited to, aziridinyl, 2H-aziridinyl, diazaziridinyl, 3H-diazacyclopropenyl, azetidinyl, 1,4-dioxanyl, 1,3-dioxanyl, 1,3-dioxolanyl, 1,4-dioxadienyl, tetrahydrofuryl, dihydropyrrolyl, pyrrolidinyl, imidazolidinyl, 4,5-dihydroimidazolyl, pyrazolidinyl, 4,5-dihydropyrazolyl, 2,5-dihydrothienyl, tetrahydrothienyl, 4,5-dihydrothiazolyl, thiazolidinyl, piperidinyl, tetrahydropyridinyl, piperidinonyl, tetrahydropyridinonyl, dihydropiperidinonyl, piperazinyl, morpholinyl, 4,5-dihydrooxazolyl, 4,5-dihydroisoxazolyl, 2,3-dihydroisoxazolyl, oxazolidinyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, 4H-1,3-thiazinyl, 6H-1,3-thiazinyl, 2H-pyranyl, 2H-pyran-2-onyl, 3,4-dihydro-2H-pyranyl and the like.

The "8-10 membered fused heterocyclyl" described herein refers to a saturated or partially saturated and non-aromatic cyclic group having 8 to 10 ring atoms and with at least one of the ring atom being a heteroatom (one ring of the fused heterocyclyl may be an aromatic ring, but the fused heterocyclyl as a whole is non-aromatic), which is formed by two or more cyclic structures sharing two adjacent atoms with each other, and the heteroatoms are nitrogen atoms, oxygen atoms and/or sulfur atoms. Optionally, a ring atom (e.g., a carbon atom, a nitrogen atom, or a sulfur atom) may be substituted by an oxo group (forming, for example, a C=O, N=O, S=O or SO$_2$ ring member). The "8-10 membered fused heterocyclyl" includes "8-9 membered fused heterocyclyl", "9-10 membered fused heterocyclyl" and the like, which may be fused in a manner as 5-6 membered heterocyclo 5-6 membered heterocyclyl, 5-6 membered heterocyclo 5-6 membered cycloalkyl, benzo 5-6 membered heterocyclyl and 5-6 membered heteroaro 5-6 membered heterocyclyl, wherein 5-6 membered heteroaryl is defined as below. Examples of "8-10 membered fused heterocyclyl" include, but are not limited to, pyrrolidinocyclopropyl, cyclopentazacyclopropyl, pyrrolidinocyclobutyl, pyrrolidinopyrrolidinyl, pyrrolidinopiperidinyl, pyrrolidinopiperazinyl, pyrrolidinomorpholinyl, piperidinomorpholinyl, benzopyrrolidinyl, tetrahydroimidazo[4,5-c]pyridinyl, 3,4-dihydroquinazolinyl, 1,2-dihydroquinoxalinyl, benzo[d][1,3]dioxolyl, 1,3-dihydroisobenzofuranyl, 2H-chromenyl, 2H-chromen-2-onyl, 4H-chromenyl, 4H-chromen-4-onyl, chromanyl, 4H-1,3-benzoxazinyl, 4,6-dihydro-1H-furo[3,4-d]imidazolyl, 3a,4,6,6a-tetrahydro-1H-furo[3,4-d]imidazolyl, 4,6-dihydro-1H-thieno[3,4-d]imidazolyl, 4,6-dihydro-1H-pyrrolo[3,4-d]imidazolyl, alkyl benzimidazolyl, octahydrobenzo[d]imidazolyl, decahydroquinolinyl, hexahydrothienoimidazolyl, hexahydrofuroimidazolyl, 4,5,6,7-tetrahydro-1H-benzo[d]imidazolyl, octahydrocyclopenta[c]pyrrolyl, dihydroindolyl, dihydroisoindolyl, benzoxazolylalkyl, benzothiazolylalkyl, 1,2,3,4-tetrahydroisoquinolinyl, 1,2,3,4-tetrahydroquinolinyl, 4H-1,3-benzoxazinyl and the like.

The "6-10 membered aryl" described herein includes "6-8 membered monocycloaryl" and "8-10 membered fused ring aryl".

The "6-8 membered monocycloaryl" described herein refers to monocycloaryl having 6 to 8 ring carbon atoms, examples of which include, but are not limited to, phenyl, cyclooctatetraenyl and the like, and preferably phenyl.

The "8-10 membered fused ring aryl" described herein refers to an aromatic cyclic group having 8 to 10 ring carbon atoms and formed by two or more cyclic structures sharing two adjacent carbon atoms with each other, and preferably "9-10 membered fused ring aryl", such as naphthyl and the like.

The "5-10 membered heteroaryl" described herein includes "5-8 membered single monoheteroaryl" and "8-10 membered fused heteroaryl".

The "5-8 membered monoheteroaryl" described herein refers to an aromatic monocyclic cyclic group having 5 to 8 ring atoms (at least one of which is a heteroatom such as a nitrogen atom, an oxygen atom or a sulfur atom). Optionally, a ring atom (e.g., a carbon atom, a nitrogen atom, or a sulfur atom) may be substituted by an oxo group (forming, for example, a C=O, N=O, S=O or $SO_2$ ring member). "5-8 membered monoheteroaryl" includes "5-7 membered monoheteroaryl", "5-6 membered monoheteroaryl", "5-6 membered nitrogen-containing monoheteroaryl", "6 membered nitrogen-containing monoheteroaryl" and the like, wherein at least one of the ring heteroatoms of the "nitrogen-containing monoheteroaryl" is a nitrogen atom, for example, it may contain only one or two nitrogen atoms, or one nitrogen atom and one or two other heteroatoms (e.g., oxygen atoms and/or sulfur atoms), or two nitrogen atoms and one or two other heteroatoms (e.g., oxygen atoms and/or sulfur atoms). Specific examples of "5-8 membered monoheteroaryl" include, but are not limited to, furyl, thienyl, pyrrolyl, thiazolyl, isothiazolyl, thiadiazolyl, oxazolyl, isoxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, 2-pyridonyl, 4-pyridonyl, pyrimidinyl, pyridazinyl, pyrazinyl, 1,2,3-triazinyl, 1,3,5-triazinyl, 1,2,4,5-tetrazinyl, azacycloheptyltrienyl, 1,3-diazacycloheptyltrienyl, azacyclooctatetraenyl and the like. Specific examples of "5-6 membered monoheteroaryl" include, but are not limited to, those having 5 to 6 ring atoms in the specific examples of the above-mentioned "5-8 membered monoheteroaryl".

The "8-10 membered fused heteroaryl" described herein refers to an aromatic cyclic structure, which is formed by two or more cyclic structures sharing two adjacent atoms with each other, and contains 8 to 10 ring atoms (at least one of which is a heteroatom such as a nitrogen atom, an oxygen atom or a sulfur atom). Optionally, a ring atom (e.g., a carbon atom, a nitrogen atom, or a sulfur atom) may be substituted by an oxo group (forming, for example, a C=O, N=O, S=O or $SO_2$ ring member). "8-10 membered fused heteroaryl" includes "9-10 membered fused heteroaryl", "8-9 membered fused heteroaryl" and the like, which may be fused in a manner as benzo 5-6 membered heteroaryl, 5-6 membered heteroaro 5-6 membered heteroaryl and the like. Specific examples of "8-10 membered fused heteroaryl" include, but are not limited to, pyrrolopyrrolyl, pyrrolofuryl, pyrazolopyrrolyl, pyrazolothienyl, furothienyl, pyrazoloxazolyl, benzofUryl, benzoisofuryl, benzothienyl, indolyl, isoindolyl, benzoxazolyl, benzoimidazolyl, indazolyl, benzotriazolyl, quinolinyl, 2-quinolinonyl, 4-quinolinonyl, 1-isoquinolinonyl, isoquinolinyl, acridinyl, phenanthridinyl, benzopyridazinyl, phthalazinyl, quinazolinyl, quinoxalinyl, purinyl, naphthyridinyl and the like.

The term "optionally substituted by . . . " described herein includes both "substituted by . . . " and "not substituted by . . . ".

The "pharmaceutically acceptable salt" described herein refers to a salt formed by an acidic functional group (e.g., —COOH, —OH, —$SO_3H$ and the like) in the compound combining with a suitable inorganic or organic base (including alkali metal salts, alkaline-earth metal salts, ammonium salts and salts with nitrogen-containing organic bases) or a salt formed by a basic functional group (e.g., —$NH_2$ and the like) in the compound combining with a suitable inorganic or organic acid (e.g., carboxylic acid and the like).

The "stereoisomer" described herein means that when the compound of the present invention can exists in a form of a racemate or a racemic mixture, a single enantiomer, a mixture of diastereoisomer or a single diastereoisomer as the compound contains one or more asymmetric centers. The compound of the present invention may have asymmetric centers and thus result in the presence of two optical isomers. The scope of the present invention includes all possible optical isomers and mixtures thereof. If the compound of the present invention contains an olefinic double bond, the scope of the present invention includes cis-isomer and trans-isomer unless otherwise specified. The compounds described herein may exist in tautomeric (one of the functional group isomers) forms having different connection points of hydrogen through one or more double bond shifts, for example, a ketone and enol form thereof are keto-enol tautomers. All tautomers and the mixture thereof are included within the scope of the present invention. All enantiomers, diastereoisomers, racemates, mesomers, cis-trans isomers, tautomers, geometric isomers and epimers of the compound as well as the mixture thereof are included in the scope of the present invention.

The "dosage form" described herein refers to a pharmaceutical form suitable for clinical use, including, but not limited to, pulvis, tablets, granules, capsules, solutions, emulsions, suspensions, injections (including injection solution, sterile powders for injection and concentrated solutions for injection), sprays, aerosols, powder spray, lotions, liniments, ointments, plasters, pastes, patches, gargles or suppositories, more preferably pulvis, tablets, granules, capsules, solutions, injections, ointments, gargles or suppositories.

All technical solutions in the references cited in present application are included within the scope of the disclosure of the present invention and are intended to be illustrate the present invention.

The advantages provided by the present invention include, but are not limited to:
1. the compound and the pharmaceutically acceptable salt, ester or stereoisomer thereof have excellent inhibition activity on one or more tyrosine kinase of TRK, ALK and/or ROS1, have good pharmacokinetic properties in vivo, lasting effect and high bioavailability, and are capable of treating and/or preventing diseases and related conditions mediated by one or more tyrosine kinases of TRK, ALK and/or ROS1;
2. the compound and the pharmaceutically acceptable salt, ester or stereoisomer thereof have better therapeutic effect on the cancer diseases mediated by one or more tyrosine kinases of TRK, ALK and/or ROS1, and especially have better therapeutic effect on the cancer diseases which have drug resistance to existing anticancer active agents; and
3. the compound of the present invention has simple preparation process and stable quality, can be prepared with high purity, and is easy for large-scale industrial production.

SUMMARY

The technical solutions of the present invention will be described below with reference to the following examples, and the above-described contents of the present invention will be further described in detail, but it should not be construed that the scope of the present invention is limited to the following examples. Any technique achieved based on the aforementioned content of the present invention shall fall within the scope of the present invention.

As used herein, a carbon atom marked with an "*" in a compound structure represents a chiral carbon atom of a single configuration, such as an R configuration or an S configuration.

In the nomenclature of compound, "2²R/S" represents that the compound is a single isomer with the configuration of the corresponding chiral carbon being "2²R" or "2²S".

Example 1: (2²R/S,6S)-3⁵-fluoro-6-methyl-1³H-4-oxa-7-aza-1(5,3)-imidazo[4,5-b]pyridina-3(3,2)-pyridina-2(1,2)-pyrrolidinacyclooctaphan-8-one (Compound2)

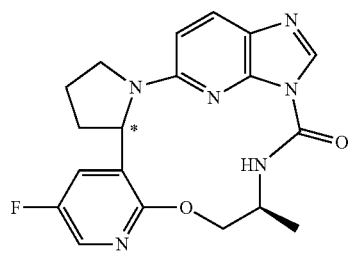 [SMILES: C[C@H]1COc2ncc(F)cc2C2CCCN2c2ccc3ncn(c3n2)C(=O)N1]

1. Preparation of 6-(2-(S-fluoro-2-methoxypyridin-3-yl)pyrrolidin-1-yl)-3-nitropyridin-2-amine

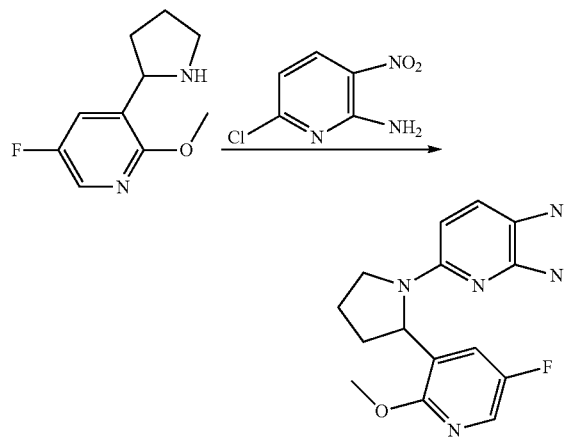

5-fluoro-2-methoxy-3-(pyrrolidin-2-yl)pyridine (2.0 g, 10.2 mmol) and 6-chloro-3-nitropyridin-2-amine (1.8 g, 10.4 mmol) were added to acetonitrile (50 mL), diisopropylethylamine (3.9 g, 30.2 mmol) was added, and the mixture was heated to 70° C. and reacted for 16 hrs. The reaction mixture was concentrated by rotary evaporation, added with water (50 mL), and filtered. The solid was washed with ethyl acetate (30 mL) and dried under vacuum to give the target product (3.2 g, yield: 94.1%).

LC-MS (M/e): 334.1 (M+H⁺)

2. Preparation of 6-(2-(5-fluoro-2-methoxypyridin-3-yl)pyrrolidin-1-yl)pyridine-2,3-diamine

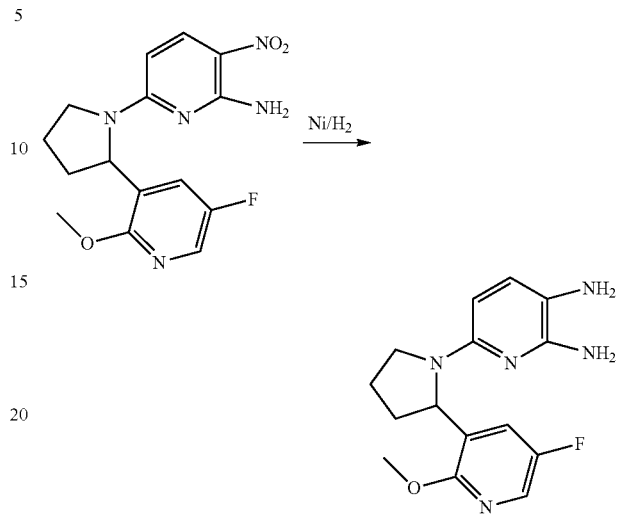

6-(2-(5-fluoro-2-methoxypyridin-3-yl)pyrrolidin-1-yl)-3-nitropyridin-2-amine (1.0 g, 3.0 mmol) was dissolved in a mixture of methanol (30 mL) and tetrahydrofuran (10 mL), raney nickel (200 mg) was added, and the mixture was reacted for 16 hrs at 25° C. under hydrogen atmosphere. The reaction mixture was filtered and concentrated by rotary evaporation, and the residue was used directly in the next step.

LC-MS (M/e): 304.1 (M+H⁺)

3. Preparation of 5-(2-(5-fluoro-2-methoxypyridin-3-yl)pyrrolidin-1-yl)-3H-imidazo[4,5-b]pyridine

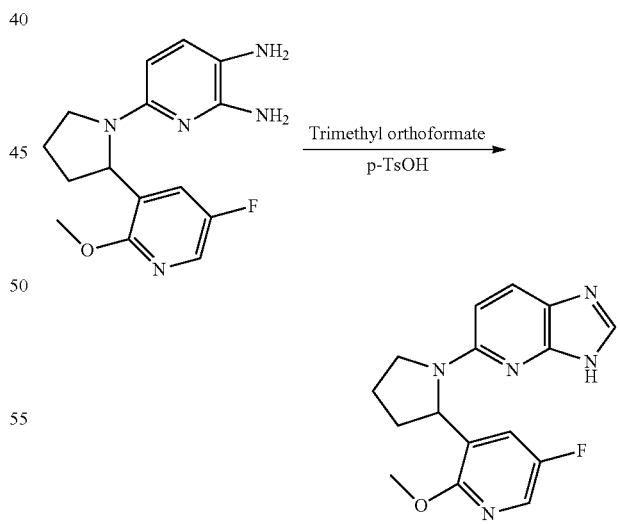

6-(2-(5-fluoro-2-methoxypyridin-3-yl)pyrrolidin-1-yl)pyridine-2,3-diamine (crude product from the above step, about 3.0 mmol) was dissolved in toluene (10 mL), triethyl orthoformate (4.4 g, 29.7 mmol) and p-toluenesulfonic acid (103 mg, 0.6 mmol) were added, and the mixture was heated to 120° C. and reacted for 4 hrs. The reaction mixture was concentrated by rotary evaporation, added with sodium bicarbonate solution (50 mL), and extracted with ethyl acetate (100 mL×3). The organic phase was combined, concentrated by rotary evaporation and purified by column chromatography (petroleum ether:ethyl acetate=1:1) to give the target product (0.85 g, yield: 90.4%).

LC-MS (M/e): 314.1 (M+H⁺)

4. Preparation of 3-(1-(3H-imidazo[4,5-b]pyridin-5-yl)pyrrolidin-2-yl)-5-fluoropyridin-2-ol

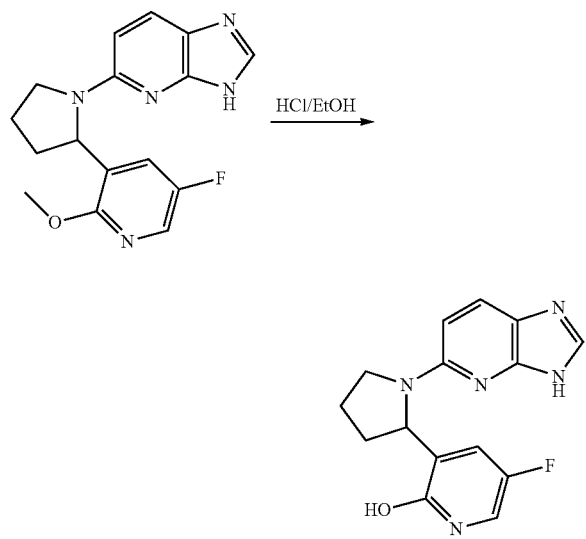

5-(2-(5-fluoro-2-methoxypyridin-3-yl)pyrrolidin-1-yl)-3H-imidazo[4,5-b]pyridine (0.85 g, 2.72 mmol) was added to a solution of hydrogen chloride in ethanol (7 mL), and the mixture was heated to 90° C. under microwave and reacted for 40 mins. The reaction mixture was concentrated by rotary evaporation, added with triethylamine (5 mL), and concentrated by rotary evaporation again. The reaction mixture was purified by medium-pressure preparative chromatography (dichloromethane:methanol=15:1) to give the target product (0.58 g, yield: 71.4%).

LC-MS (M/e): 300.1 (M+H⁺)

5. Preparation of tert-butyl ((2S)-1-((3-(1-(3H-imidazo[4,5-b]pyridin-S-yl)pyrrolidin-2-yl)-5-fluoropyridin-2-yl)oxy)propan-2-yl)carbamate

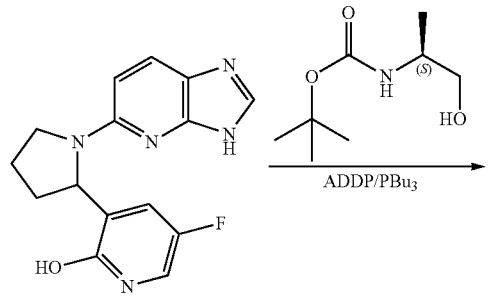

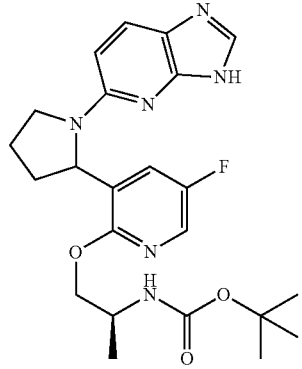

3-(1-(3H-imidazo[4,5-b]pyridin-5-yl)pyrrolidin-2-yl)-5-fluoropyridin-2-ol (300 mg, 1.0 mmol) and tert-butyl (S)-(1-hydroxyprop-2-yl) carbamate (350 mg, 2.0 mmol) were added to tetrahydrofuran (10 mL), azobisformyl dipiperidine (630 mg, 2.5 mmol) and tri-n-butylphosphine (510 mg, 2.5 mmol) were added, and the mixture was reacted at 50° C. for 16 hrs. The reaction mixture was concentrated by rotary evaporation and purified by column chromatography (dichloromethane:methanol=30:1) to give the target product (340 mg, yield: 74.4%).

LC-MS (M/e): 457.0 (M+H⁺)

6. Preparation of (2S)-1-((3-(1-(3H-imidazo[4,5-b]pyridin-5-yl)pyrrolidin-2-yl)-5-fluoropyridin-2-yl)oxy) propan-2-amine

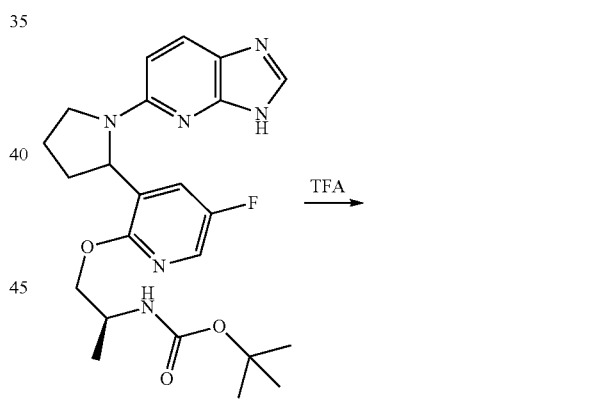

Tert-butyl ((2S)-1-((3-(1-(3H-imidazo[4,5-b]pyridin-5-yl)pyrrolidin-2-yl)-5-fluoropyridin-2-yl)oxy) propan-2-yl) carbamate (0.30 g, 0.66 mmol) was dissolved in dichloromethane (20 mL), trifluoroacetic acid (3 mL) was added, and the mixture was reacted at 25° C. for 16 hrs. The reaction mixture was concentrated by rotary evaporation, and the residue was used directly in the next step.

LC-MS (M/e): 357.0 (M+H⁺)

7. Preparation of (6S)-3⁵-fluoro-6-methyl-1³H-4-oxa-7-aza-1(5,3)-imidazo[4,5-b]pyridina-3(3,2)-pyridina-2(1,2)-pyrrolidinacyclooctaphan-8-one (Compound 2-1)

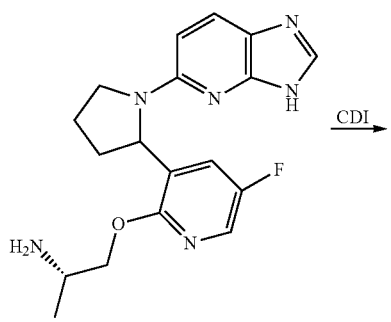

A solution of (2S)-1-((3-(1-(3H-imidazo[4,5-b]pyridin-5-yl)pyrrolidin-2-yl)-5-fluoropyridin-2-yl)oxy) propan-2-amine (crude product from the above step, about 0.66 mmol) and triethylamine (2 mL) in tetrahydrofuran (10 mL) was added dropwise to a solution of carbonyldiimidazole (160 mg, 1.0 mmol) in tetrahydrofuran (10 mL), and the mixture was reacted at 25° C. for 4 hrs. The reaction mixture was concentrated by rotary evaporation and purified by medium-pressure preparative chromatography (dichloromethane:methanol=20:1) to give the target product (crude, 300 mg).

LC-MS (M/e): 383.2 (M+H⁺)

8. Preparation of (2²R/S,6S)-3⁵-fluoro-6-methyl-1³H-4-oxa-7-aza-1(5,3)-imidazo[4,5-b]pyridina-3(3,2)-pyridina-2(1,2)-pyrrolidinacyclooctaphan-8-one (Compound 2)

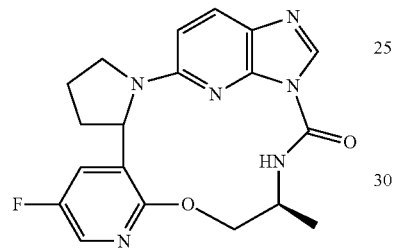

(6S)-3⁵-fluoro-6-methyl-1³H-4-oxa-7-aza-1(5,3)-imidazo[4,5-b]pyridina-3(3,2)-pyridina-2(1,2)-pyrroli dinacyclooctaphan-8-one (crude) was separated by high-pressure preparative chromatography (acetonitrile:water=7:3) to give the title compound (50 mg, 7-9 three-step yield: 19.9%).

The title compound was prepared as a 1.12 mg/mL methanol solution and the specific rotation of the title compound was −47.62 according to the 0621 Optical Rotation Determination Method of General Chapter IV, *Chinese Pharmacopoeia*, 2015 Edition.

Molecular formula: $C_{19}H_{19}FN_6O_2$

Molecular weight: 382.4

LC-MS (M/e): 383.2 (M+H⁺)

¹H-NMR (400 MHz, CDCl₃) δ 10.01 (s, 1H), 8.38 (s, 1H), 7.88 (d, J=10.4 Hz, 1H), 7.87 (s, 1H), 7.35-7.38 (m, 1H), 6.51 (d, J=9.2 Hz, 1H), 5.67-5.70 (m, 1H), 5.11-5.14 (m, 1H), 4.28-4.32 (m, 1H), 4.22-4.26 (m, 1H), 3.90-3.96 (m, 1H), 3.53-3.59 (m, 1H), 2.41-2.49 (m, 2H), 2.32-2.23 (m, 1H), 1.92-1.95 (m, 1H), 1.59 (d, J=6.8 Hz, 3H).

Example 2: (2²R/S,6R)-3⁵-fluoro-6-methyl-1³H-4-oxa-7-aza-1(5,3)-imidazo[4,5-b]pyridina-3(3,2)-pyridina-2(1,2)-pyrrolidinacyclooctaphan-8-one (Compound 3)

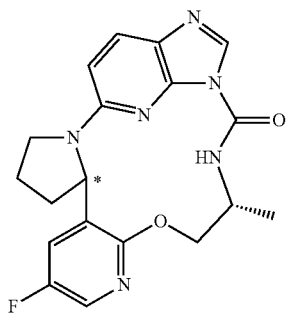

1. Preparation of 3-(1-(3H-imidazo[4,5-b]pyridin-5-yl)pyrrolidin-2-yl)-5-fluoropyridin-2-ol

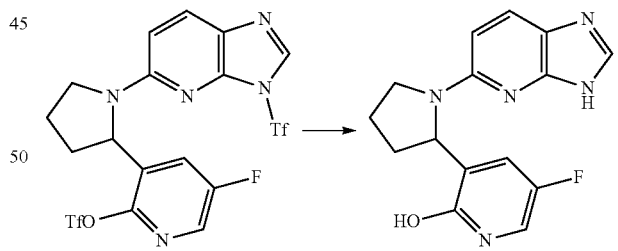

5-fluoro-3-(1-(3-(trifluoromethanesulfonyl)-3H-imidazo[4,5-b]pyridin-5-yl)pyrrolidin-2-yl]pyridin-2-yl trifluoromethanesulfonate (900 mg, 1.6 mmol) was dissolved in tetrahydrofuran (16 mL) and water (5 mL), lithium hydroxide monohydrate (335.2 mg, 7.99 mmol) was added, and the mixture was reacted at 25° C. for 16 hrs. The reaction mixture was adjusted to pH 6 with hydrochloric acid and extracted with ethyl acetate (30 mL). The organic phase was washed with saturated brine (15 mL), dried over anhydrous sodium sulfate, and concentrated to give the target product (360 mg, yield: 75%).

LC-MS (M/e): 300.1 (M+H⁺)

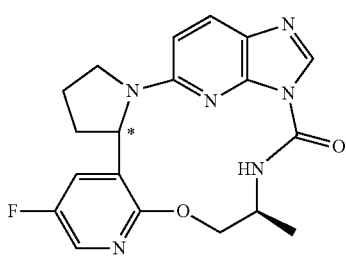 [SMILES: C[C@H]1COc2ncc(F)cc2C2CCCN2c2ccc3ncn(c3n2)C(=O)N1]

2. Preparation of tert-butyl ((2R)-(1-((3-(1-(3H-imidazo[4,5-b]pyridin-S-yl)pyrrolidin-2-yl)-5-fluoropyridin-2-yl)oxy)propan-2-yl)carbamate

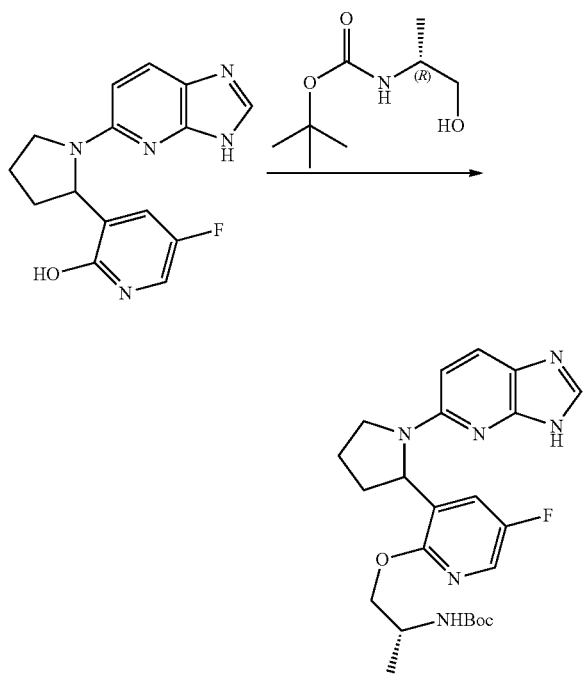

3-(1-(3H-imidazo[4,5-b]pyridin-5-yl)pyrrolidin-2-yl)-5-fluoropyridin-2-ol (360 mg, 1.2 mmol), (R)-(1-hydroxypropan-2-yl)carbamic acid tert-butyl ester (316.1 mg, 1.8 mmol), azobisformyl dipiperidine (455.2 mg, 1.8 mmol) and tri-n-butylphosphine (365 mg, 1.8 mmol) were dissolved in tetrahydrofuran (6 mL), and the mixture was reacted for 16 hrs at 50° C. under nitrogen atmosphere. The reaction mixture was concentrated and purified by column chromatography (5% methanol/dichloromethane) to give the target product (280 mg, yield: 51%).

LC-MS (M/e): 457.0 (M+H⁺)

3. Preparation of (2R)-1-((3-(1-(3H-imidazo[4,5-b]pyridin-5-yl)pyrrolidin-2-yl)-5-fluoropyridin-2-yl)oxy)propan-2-amine

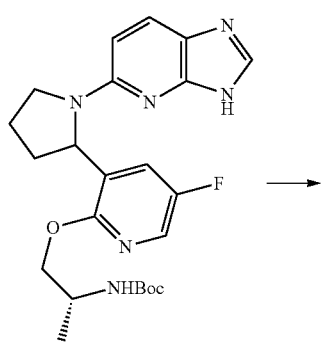

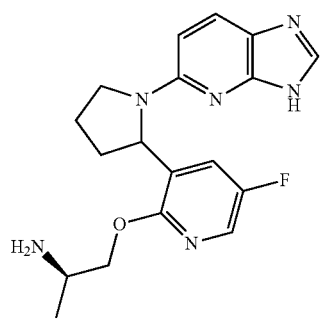

Tert-butyl ((2R)-(1-((3-(1-(3-imidazo[4,5-b]pyridin-5-yl) pyrrolidin-2-yl)-5-fluoropyridin-2-yl)oxy) propan-2-yl) carbamate (280 mg, 0.61 mmol) was dissolved in dichloromethane (30 mL), trifluoroacetic acid (3 mL) was added, and the mixture was reacted at 25° C. for 0.5 hr. The reaction mixture was concentrated by rotary evaporation, and the residue was used directly in the next step.

LC-MS (M/e): 357.0 (M+H⁺)

4. Preparation of (6R)-3⁵-fluoro-6-methyl-1³H-4-oxa-7-aza-1(5,3)-imidazo[4,5-b]pyridina-3(3,2)-pyridina-2(1,2)-pyrrolidinacyclooctaphan-8-one (Compound 3-1)

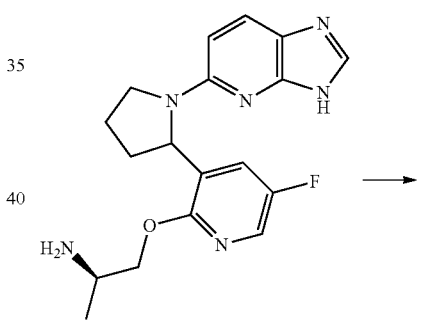

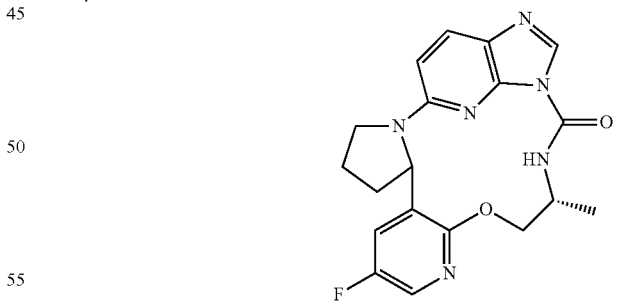

A solution of (2R)-(1-((3-(1-(3H-imidazo[4,5-b]pyridin-5-yl)pyrrolidin-2-yl)-5-fluoropyridin-2-yl)-oxy) propan-2-amine (crude product from the above step, about 0.61 mmol) in tetrahydrofuran (10 mL) and triethylamine (2 mL) were added to a solution of carbonyldiimidazole (149.2 mg, 0.92 mmol) in tetrahydrofuran (10 mL), and the mixture was reacted at 25° C. for 16 hrs. The reaction mixture was concentrated to give the target product (crude).

LC-MS (M/e): 383.2 (M+H⁺)

5. Preparation of (2²R/S,6R)-3⁵-fluoro-6-methyl-1³H-4-oxa-7-aza-1(5,3)-imidazo[4,5-b]pyridina-3(3,2)-pyridina-2(1,2)-pyrrolidinacyclooctaphan-8-one (Compound 3)

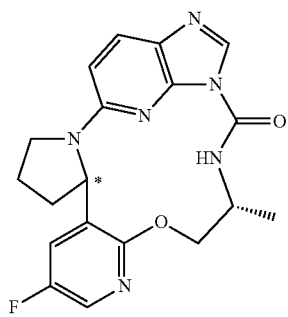 [SMILES: C[C@@H]1COc2ncc(F)cc2C2CCCN2c2ccc3ncn(c3n2)C(=O)N1]

(6R)-3⁵-fluoro-6-methyl-1³H-4-oxa-7-aza-1(5,3)-imidazo[4,5-b]pyridina-3(3,2)-pyridina-2(1,2)-pyrrol idinacyclooctaphan-8-one (crude) was separated by high-pressure reversed-phase column chromatography (acetonitrile:water=7:3) to give the title compound (12 mg, 3-5 three-step yield: 5.1%).

Molecular formula: C₁₉H₁₉FN₆O₂
Molecular weight: 382.4
LC-MS (M/e): 383.0 (M+H⁺)
¹H-NMR (400 MHz, CDCl₃) 1510.50 (d, J=7.6 Hz, 1H), 8.35 (s, 1H), 7.89-7.84 (m, 2H), 7.34-7.26 (m, 1H), 6.50 (d, J=8.8 Hz, 1H), 5.63-5.60 (m, 1H), 5.16-5.12 (m, 1H), 4.45-4.35 (m, 1H), 4.18-4.13 (m, 1H), 3.95-3.92 (m, 1H), 3.62-3.59 (m, 1H), 2.54-2.42 (m, 2H), 2.26-2.23 (m, 1H), 1.99-1.96 (m, 1H), 1.56 (d, J=8.8 Hz, 3H).

Example 3: (2²R/S,6R)-3⁵-fluoro-6-methyl-1³H-7-aza-1(5,3)-imidazo[4,5-b]pyridina-3(3,2)-pyridina-2(1,2)-pyrrolidinacyclooctaphan-8-one (Compound 11)

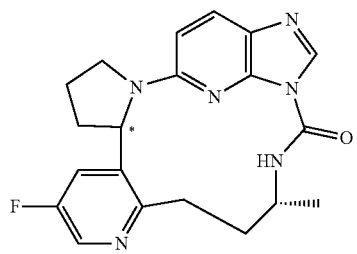 [SMILES: C[C@@H]1CCc2ncc(F)cc2C2CCCN2c2ccc3ncn(c3n2)C(=O)N1]

1. Preparation of benzyl (R)-but-3-yn-2-yl((2-nitrophenyl)sulfonyl)carbamate

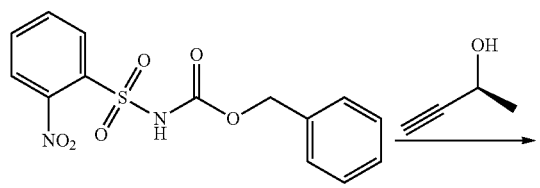

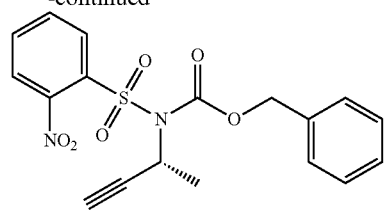

Benzyl ((2-nitrophenyl)sulfonyl)carbamate (5.0 g, 14.9 mmol) and (S)-but-3-yn-2-ol (1.0 g, 14.3 mmol) were dissolved in tetrahydrofuran (60 mL), and triphenylphosphine (4.0 g, 15.2 mmol) was added. Diethyl azodicarboxylate (2.7 g, 15.5 mmol) was added under nitrogen atmosphere, and the mixture was reacted at 20° C. for 16 hrs. The reaction mixture was concentrated and purified by column chromatography (petroleum ether:ethyl acetate=2:1) to give the target product (3.16 g, yield: 56.9%).

LC-MS (M/e): 389.0 (M+H⁺)

2. Preparation of benzyl (R)-but-3-yn-2-yl carbamate

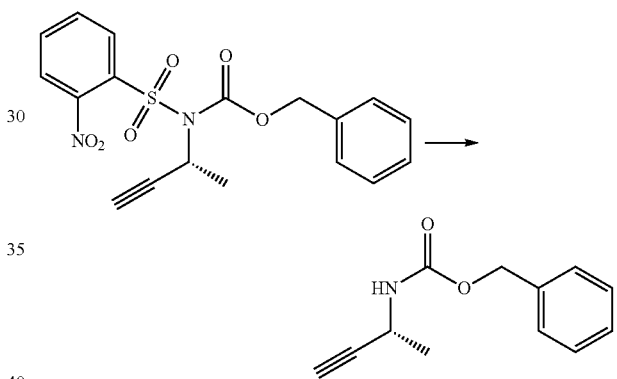

Benzyl (R)-but-3-yn-2-yl((2-nitrophenyl)sulfonyl)carbamate (3.16 g, 8.14 mmol) was dissolved in N,N-dimethylformamide (30 mL), and lithium hydroxide (2.4 g, 57.1 mmol) and thioglycolic acid (2.6 g, 28.3 mmol) were added, and the mixture was reacted at 20° C. for 16 hrs. The reaction mixture was added with water (100 mL) and ethyl acetate (100 mL) and separated, and the aqueous phase was extracted with ethyl acetate (100 mL×3). The organic phase was combined, concentrated and purified by column chromatography (petroleum ether:ethyl acetate=10:1) to give the target product (890 mg, yield: 53.9%).

LC-MS (M/e): 204.1 (M+H⁺)

3. Preparation of 6-(2-(S-fluoro-2-methoxypyridin-3-yl)pyrrolidin-1-yl)-3-nitropyridin-2-amine

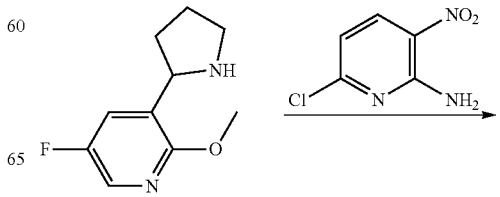

5. Preparation of 5-(2-(5-fluoro-2-methoxypyridin-3-yl)pyrrolidin-1-yl)-3H-imidazo[4,5-b]pyridine

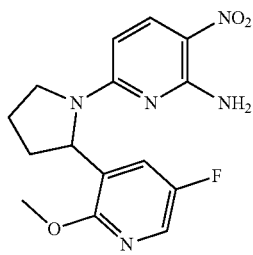

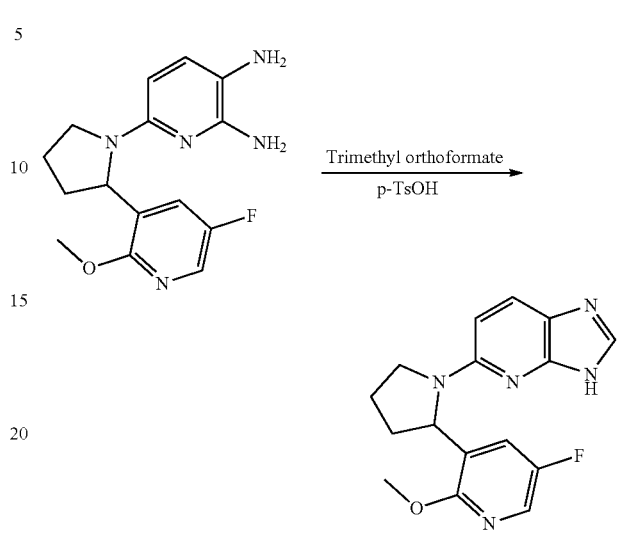

5-fluoro-2-methoxy-3-(pyrrolidin-2-yl)pyridine (2.0 g, 10.2 mmol) and 6-chloro-3-nitropyridin-2-amine (1.8 g, 10.4 mmol) were added to acetonitrile (50 mL), diisopropylethylamine (3.9 g, 30.2 mmol) was added, and the mixture was heated to 70° C. and reacted for 16 hrs. The reaction mixture was concentrated by rotary evaporation, added with water (50 mL) and filtered; the solid was washed with ethyl acetate (30 mL) and dried under vacuum to give the target product (3.2 g, yield: 94.1%).

LC-MS (M/e): 334.1 (M+H$^+$)

4. Preparation of 6-(2-(5-fluoro-2-methoxypyridin-3-yl)pyrrolidin-1-yl)pyridine-2,3-diamine

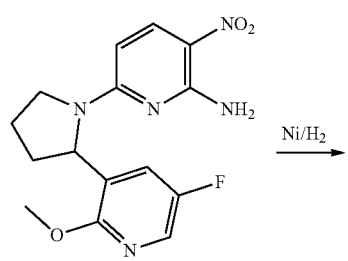

6-(2-(5-fluoro-2-methoxypyridin-3-yl)pyrrolidin-1-yl)pyridine-2,3-diamine (crude product from the above step, about 3.0 mmol) was dissolved in toluene (10 mL), triethyl orthoformate (4.4 g, 29.7 mmol) and p-toluenesulfonic acid (103 mg, 0.6 mmol) were added, and the mixture was heated to 120° C. and reacted for 4 hrs. The reaction mixture was concentrated by rotary evaporation, added with sodium bicarbonate solution (50 mL), and extracted with ethyl acetate (100 mL×3). The organic phase was combined, concentrated by rotary evaporation and purified by column chromatography (petroleum ether:ethyl acetate=1:1) to give the target product (0.85 g, yield: 90.4%).

LC-MS (M/e): 314.1 (M+H$^+$)

6. Preparation of 3-(1-(3H-imidazo[4,5-b]pyridin-5-yl)pyrrolidin-2-yl)-5-fluoropyridin-2-ol

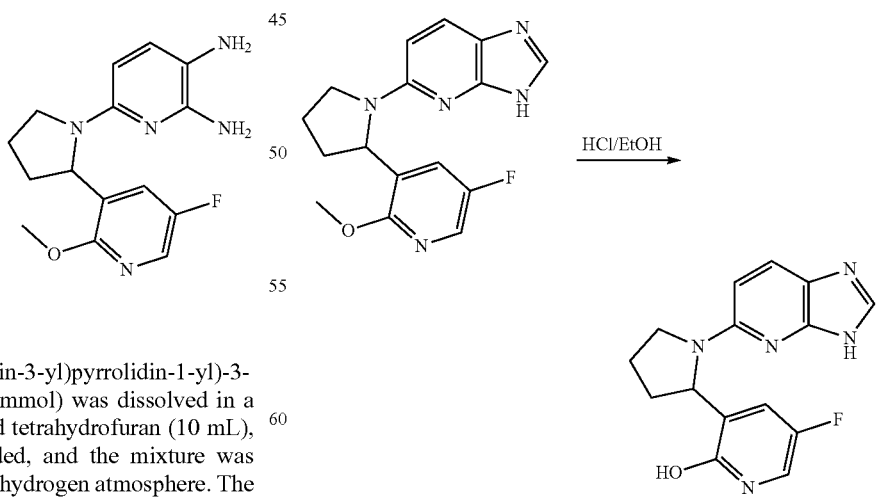

6-(2-(5-fluoro-2-methoxypyridin-3-yl)pyrrolidin-1-yl)-3-nitropyridin-2-amine (1.0 g, 3.0 mmol) was dissolved in a mixture of methanol (30 mL) and tetrahydrofuran (10 mL), raney nickel (200 mg) was added, and the mixture was reacted for 16 hrs at 25° C. under hydrogen atmosphere. The reaction mixture was filtered and concentrated by rotary evaporation, and the residue was used directly in the next step.

LC-MS (M/e): 304.1 (M+H$^+$)

5-(2-(5-fluoro-2-methoxypyridin-3-yl)pyrrolidin-1-yl)-3H-imidazo[4,5-b]pyridine (0.85 g, 2.72 mmol) was added to a solution of hydrogen chloride in ethanol (7 mL), and the mixture was heated to 90° C. under microwave and reacted for 40 mins. The reaction mixture was concentrated by rotary evaporation, added with triethylamine (5 mL), and concentrated by rotary evaporation again. The reaction mixture was purified by medium-pressure preparative chromatography (dichloromethane:methanol=15:1) to give the target product (0.58 g, yield: 71.4%).

LC-MS (M/e): 300.1 (M+H⁺)

7. Preparation of 5-fluoro-3-(1-(3-((trifluoromethyl)sulfonyl)-3H-imidazo[4,5-b]pyridin-5-yl)pyrrolidin-2-yl)pyridin-2-yl trifluoromethanesulfonate

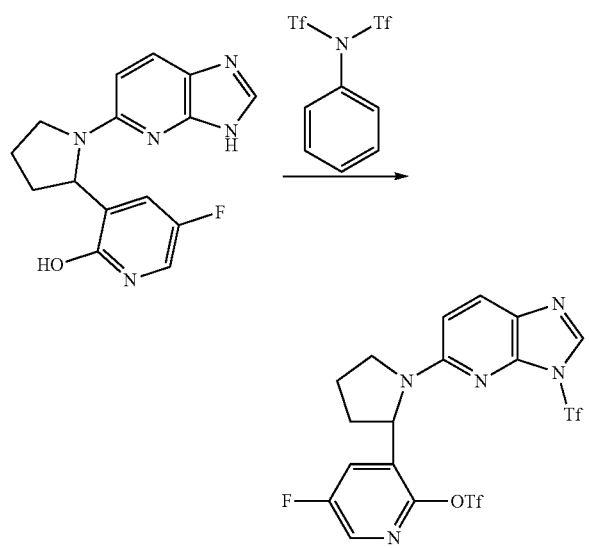

3-(1-(3H-imidazo[4,5-b]pyridin-5-yl)pyrrolidin-2-yl)-5-fluoropyridin-2-ol (0.58 g, 1.94 mmol) was dissolved in dichloromethane (20 mL), 1,1,1-trifluoro-N-phenyl-N-((trifluoromethyl)sulfonyl) methanesulfonamide (2.1 g, 5.88 mmol) and triethylamine (784 mg, 7.76 mmol) were added, and the mixture was reacted at 20° C. for 16 hrs. The reaction mixture was concentrated by rotary evaporation and purified by column chromatography (petroleum ether:ethyl acetate=2:1) to give the target product (0.73 g, yield: 67.0%).

LC-MS (M/e): 564.0 (M+H⁺)

8. Preparation of benzyl ((2R)-4-(5-fluoro-3-(1-(3-((trifluoromethyl)sulfonyl)-3H-imidazo[4,5-b]pyridin-5-yl)pyrrolidin-2-yl)pyridin-2-yl)-but-3-yn-2-yl)carbamate

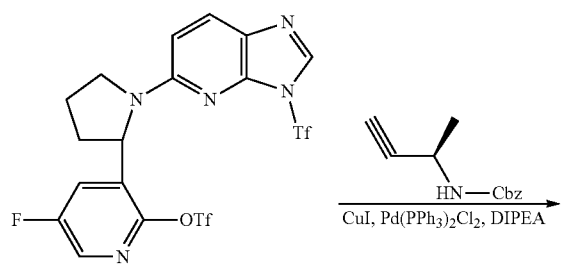

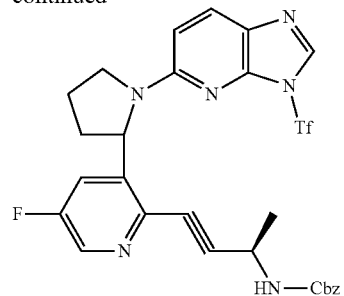

5-fluoro-3-(1-(3-((trifluoromethyl)sulfonyl)-3H-imidazo[4,5-b]pyridin-5-yl)pyrrolidin-2-yl)pyridin-2-yl trifluoromethanesulfonate (0.73 g, 1.3 mmol), cuprous iodide (50 mg, 0.26 mmol), bis(triphenylphosphine)palladium(II) dichloride (91 mg, 0.13 mmol) and N,N-diisopropylethylamine (503 mg, 3.9 mmol) were dissolved in tetrahydrofuran (50 mL), and the mixture was reacted for 0.5 hr at 50° C. under nitrogen atmosphere. A solution of benzyl (R)-but-3-yn-2-yl carbamate (300 mg, 1.5 mmol) in tetrahydrofuran was added slowly, and the mixture was reacted at 50° C. for 4 hrs. The reaction mixture was concentrated by rotary evaporation and purified by column chromatography (petroleum ether:ethyl acetate=1:1) to give the target product (0.53 g, yield: 66.3%).

LC-MS (M/e): 617.2 (M+H⁺)

9. Preparation of benzyl ((2R)-4-(3-(1-(3H-imidazo[4,5-b]pyridin-5-yl)pyrrolidin-2-yl)-5-fluoropyridin-2-yl)-but-3-yn-2-yl)carbamate

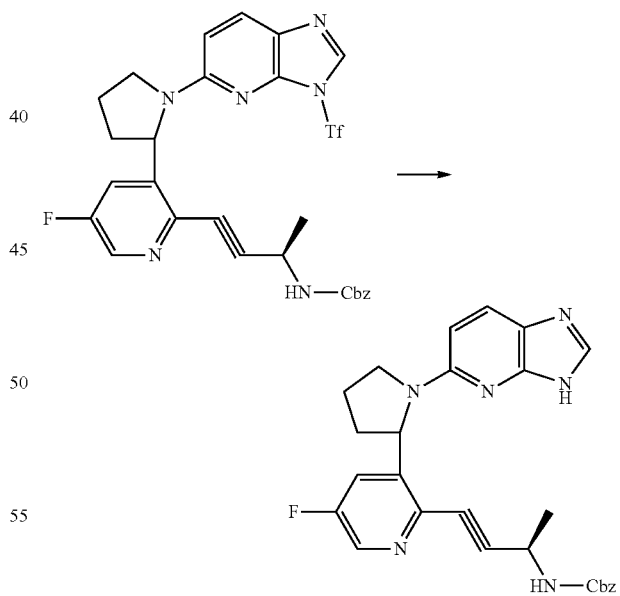

Benzyl ((2R)-4-(5-fluoro-3-(1-(3-((trifluoromethyl)sulfonyl)-3H-imidazo[4,5-b]pyridin-5-yl)pyrrolidin-2-yl)pyridin-2-yl)-but-3-yn-2-yl)carbamate (0.53 g, 0.86 mmol) was dissolved in tetrahydrofuran (20 mL) and water (20 mL), lithium hydroxide (180 mg, 4.3 mmol) was added, and the mixture was reacted at 20° C. for 1 hr. The reaction mixture was added with ethyl acetate (20 mL) and separated, and the aqueous phase was extracted with ethyl acetate (20 mL×2).

The organic phase was combined, concentrated and purified by column chromatography (dichloromethane:methanol=20:1) to give the target product (0.4 g, yield: 96.2%).

LC-MS (M/e): 485.2 (M+H⁺)

10. Preparation of (2R)-4-(3-(1-(3H-imidazo[4,5-b]pyridin-5-yl)pyrrolidin-2-yl)-5-fluoropyridin-2-yl)butan-2-amine

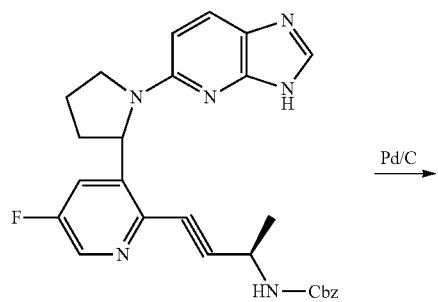

Benzyl ((2R)-4-(3-(1-(3H-imidazo[4,5-b]pyridin-5-yl)pyrrolidin-2-yl)-5-fluoropyridin-2-yl)-but-3-yn-2-yl)carbamate (0.4 g, 0.83 mmol) was dissolved in methanol (50 mL), Palladium on Carbon (200 mg) was added, and the mixture was reacted for 16 hrs at 20° C. under hydrogen atmosphere. The reaction mixture was filtered, the filtrate was concentrated to give the target product (crude) which was used directly in the next step without purification.

LC-MS (M/e): 355.2 (M+H⁺)

11. Preparation of (6R)-3⁵-fluoro-6-methyl-1³H-7-aza-1(5,3)-imidazo[4,5-b]pyridina-3(3,2)-pyridina-2(1,2)-pyrrolidinacyclooctaphan-8-one (Compound 11-1)

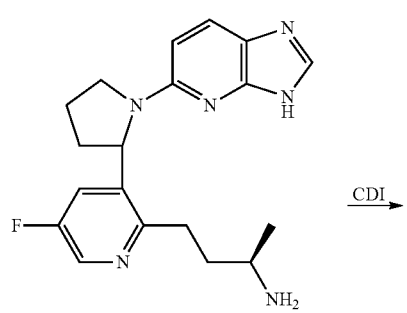

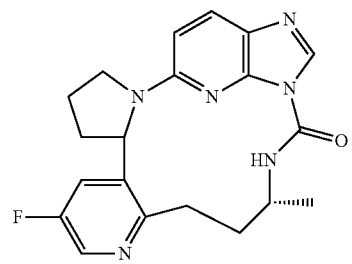

N,N'-carbonyldiimidazole (250 mg, 1.54 mmol) was dissolved in tetrahydrofuran (20 mL), and then added to a solution of (2R)-4-(3-(1-(3H-imidazo[4,5-b]pyridin-5-yl)pyrrolidin-2-yl)-5-fluoropyridin-2-yl) butan-2-amine (crude product from the above step) in tetrahydrofuran (10 mL), and the mixture was reacted at 25° C. for 2 hrs. The reaction mixture was concentrated and purified by column chromatography (dichloromethane:methanol=20:1) to give the target product (crude, 40 mg).

12. Preparation of (2²R/S,6R)-3⁵-fluoro-6-methyl-1³H-7-aza-1(5,3)-imidazo[4,5-b]pyridina-3(3,2)-pyridina-2(1,2)-pyrrolidina cyclooctaphan-8-one (Compound 11)

(6R)-3⁵-fluoro-6-methyl-1³H-7-aza-1(5,3)-imidazo[4,5-b]pyridina-3(3,2)-pyridina-2(1,2)-pyrrolidinac yclooctaphan-8-one (crude) was separated by high-pressure preparative chromatography (acetonitrile:water=8:2) to give the title compound (3 mg, 10-12 three-step yield: 0.95%).

Molecular formula: $C_{20}H_{21}FN_6O$

Molecular weight: 380.4

LC-MS (M/e): 381.1 (M+H⁺)

¹H-NMR (400 MHz, CDCl₃) δ 9.46 (d, J=8.0 Hz, 1H), 8.33 (s, 1H), 8.30 (d, J=2.8 Hz, 1H), 7.88 (d, J=8.8 Hz, 1H), 7.14 (dd, J=2.8 Hz, 9.6 Hz, 1H), 6.53 (d, J=8.8 Hz, 1H), 5.42 (t, J=6.0 Hz, 1H), 4.35-4.37 (m, 1H), 3.91-3.96 (m, 1H), 3.68-3.71 (m, 1H), 3.39-3.43 (m, 1H), 2.87-2.92 (m, 2H), 2.51-2.54 (m, 1H), 2.34-2.38 (m, 1H), 2.18-2.25 (m, 2H), 2.00-2.02 (m, 1H), 1.83-1.88 (m, 1H), 1.39 (d, J=6.8 Hz, 3H).

Example 4: (3R,7S)-4$^5$-fluoro-3,7-dimethyl-1$^3$H-5-oxa-2,8-diaza-1(5,3)-imidazo[4,5-b]pyridina-4(3,2)-pyridinacyclononphan-9-one (Compound 13)

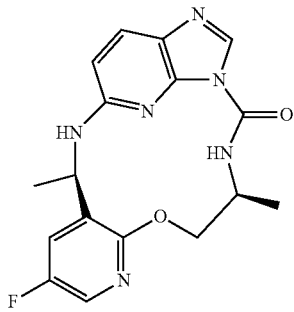 [SMILES: C[C@H]1COc2ncc(F)cc2[C@@H](C)Nc2ccc3ncn(c3n2)C(=O)N1]

1. Preparation of 3-(1-((3H-imidazo[4,5-b]pyridin-5-ylamino)ethyl)-5-fluoropyridin-2-ol

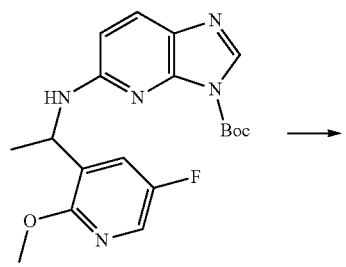

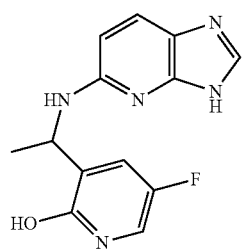

Tert-butyl 5-((1-(5-fluoro-2-methoxypyridin-3-yl)ethyl)amino)-3H-imidazo[4,5-b]pyridine-3-carboxylate (400 mg, 104 mmol) was dissolved in a solution of hydrogen chloride in ethanol (6 mL), and the mixture was reacted at 85° C. for 16 hrs. The reaction mixture was concentrated by rotary evaporation, adjusted to pH 8 with triethylamine, and purified by reversed-phase column chromatography (0-20% acetonitrile/water) to give the target product (100 mg, yield: 35%).

LC-MS (M/e): 274.0 (M+H$^+$)

2. Preparation of Tert-butyl ((2S)-1-((3-(1-((3H-imidazo[4,5-b]pyridin-5-yl)amino)ethyl)-5-fluoro-pyridin-2-yl)oxy))propan-2-yl)carbamate

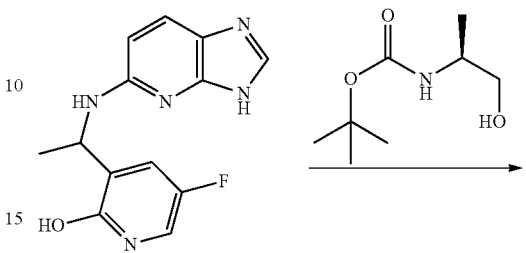

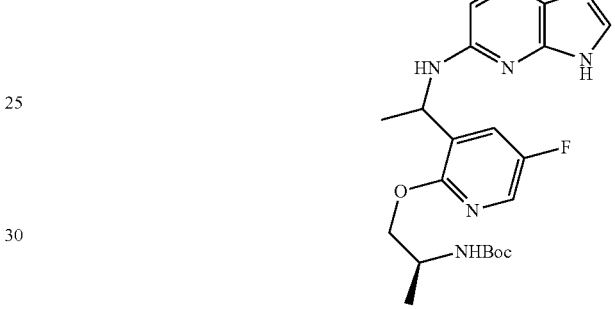

3-(1-((3H-imidazo[4,5-b]pyridin-5-yl amino)ethyl)-5-fluoropyridin-2-ol (100 mg, 0.37 mmol), tert-butyl (S)-(1-hydroxypropan-2-yl)carbamate (96.2 mg, 0.55 mmol), azobisformyl dipiperidine (138.5 mg, 0.55 mmol) and tri-n-butylphosphine (111.1 mg, 0.55 mmol) were dissolved in tetrahydrofuran (2 mL), and the mixture was reacted for 16 hrs at 50° C. under nitrogen atmosphere. The reaction mixture was concentrated and purified by column chromatography (5% methanol/dichloromethane) to give the target product (40 mg, yield: 25%).

LC-MS (M/e): 431.0 (M+H$^+$)

3. Preparation of N-(1-(2-((S)-2-aminopropoxy)-5-fluoropyridin-3-yl)ethyl)-3H-imidazo[4,5-b]pyridin-5-amine

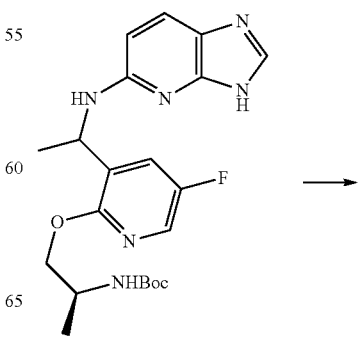

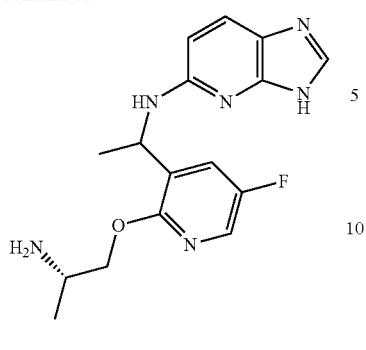

Tert-butyl ((2S)-1-((3-(1-((3H-imidazo[4,5-b]pyridin-5-yl)amino)ethyl)-5-fluoropyridin-2-yl)oxy)) propan-2-yl)carbamate (40 mg, 0.093 mmol) was dissolved in dichloromethane (2 mL), trifluoroacetic acid (1 mL) was added, and the mixture was reacted for 0.5 hr. The reaction mixture was concentrated and the crude product was used directly in the next step.

LC-MS (M/e): 331.0 (M+H$^+$)

4. Preparation of (7S)-4$^5$-fluoro-3,7-dimethyl-1$^3$H-5-oxa-2,8-diaza-1(5,3)-imidazo[4,5-b]pyridina-4(3,2)-pyridinacyclononphan-9-one (Compound 13-1)

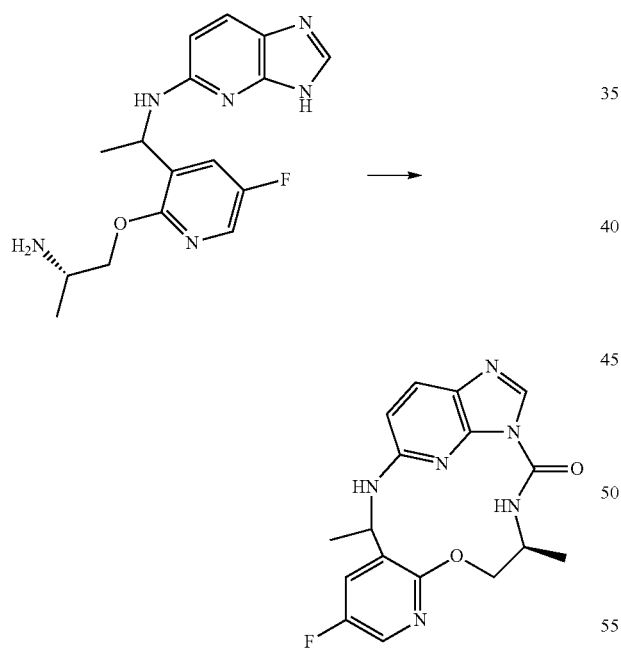

A solution of N-(1-(2-((S)-2-aminopropoxy)-5-fluoropyridin-3-yl)ethyl)-3H-imidazo[4,5-b]pyridin-5-amine (crude product from the above step) in tetrahydrofuran (1 mL) and triethylamine (0.2 mL) were added to a solution of carbonyldiimidazole (22.6 mg, 0.14 mmol) in tetrahydrofuran (1 mL), and the mixture was reacted at 25° C. for 16 hrs. The reaction mixture was concentrated to give the target product (crude).

LC-MS (M/e): 357.1 (M+H$^+$)

5. Preparation of (3R,7S)-4$^5$-fluoro-3,7-dimethyl-1$^3$H-5-oxa-2,8-diaza-1(5,3)-imidazo[4,5-b]pyridina-4(3,2)-pyridinacyclononphan-9-one (Compound 13)

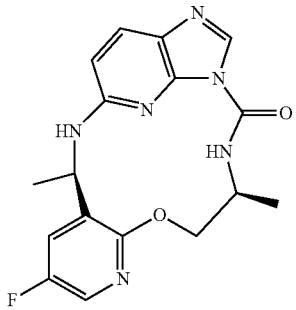 [SMILES: C[C@H]1COc2ncc(F)cc2[C@@H](C)Nc2ccc3ncn(c3n2)C(=O)N1]

(7S)-4$^5$-fluoro-3,7-dimethyl-1$^3$H-5-oxa-2,8-diaza-1(5,3)-imidazo[4,5-b]pyridina-4(3,2)-pyridinacyclononphan-9-one was separated by high-pressure reversed-phase column chromatography (acetonitrile/water=70%) to give the title compound (3 mg, 3-5 three-step yield: 9%).

The title compound was prepared as a 1.12 mg/mL methanol solution and the specific rotation of the title compound was +175.3 according to the 0621 Optical Rotation Determination Method of General Chapter IV, Chinese Pharmacopoeia, 2015 Edition.

Molecular formula: $C_{17}H_{17}FN_6O_2$

Molecular weight: 356.4

LC-MS (M/e): 357.1 (M+H$^+$)

$^1$H-NMR (400 MHz, CDCl$_3$) δ10.28 (s, 1H), 8.37 (s, 1H), 7.88 (d, J=2.8, 1H), 7.79 (d, J=8.8, 1H), 7.48-7.44 (m, 1H), 6.43 (d, J=8.8, 1H), 5.56-5.53 (m, 1H), 5.06-5.03 (m, 1H), 4.92-4.89 (m, 1H), 4.31-4.25 (m, 2H), 1.63 (d, J=6.4, 3H), 1.53 (d, J=6.8, 3H).

Example 5: (2$^2$R,6R)-3$^5$-fluoro-6-methyl-1$^3$H-4-oxa-7-aza-1(5,3)-imidazo[4,5-b]pyridina-3(3,2)-pyridina-2(1,2)-pyrrolidinacyclooctaphan-8-one (Compound 3')

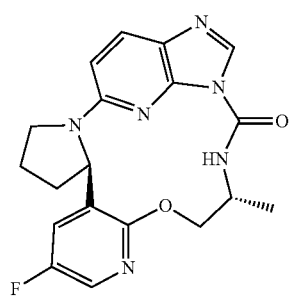 [SMILES: C[C@@H]1COc2ncc(F)cc2[C@H]2CCCN2c2ccc3ncn(c3n2)C(=O)N1]

1. Preparation of (R)-6-(2-(S-fluoro-2-methoxypyridin-3-yl)pyrrolidin-1-yl)-3-nitropyridin-2-amine

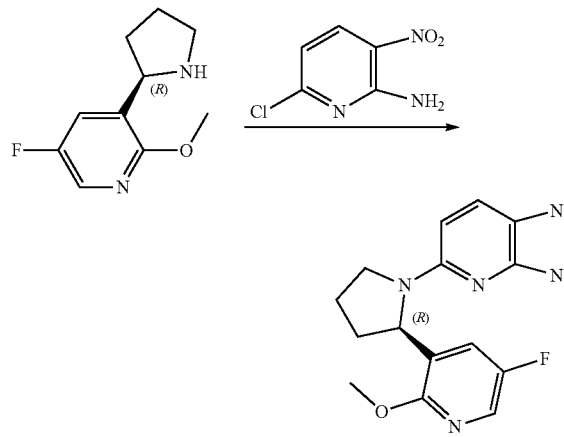

(R)-5-fluoro-2-methoxy-3-(pyrrolidin-2-yl)pyridine (1.0 g, 5.1 mmol) and 6-chloro-3-nitropyridin-2-amine (886 mg, 5.1 mmol) were added to acetonitrile (30 mL), diisopropylethylamine (1.98 g, 15.3 mmol) was added, and the mixture was heated to 70° C. and reacted for 16 hrs. The reaction mixture was concentrated by rotary evaporation, added with water (30 mL), and filtered. The solid was washed with ethyl acetate (30 mL) and dried under vacuum to give the target product (1.65 g, yield: 97.0%).

LC-MS (M/e): 334.1 (M+H$^+$)

2. Preparation of (R)-6-(2-(S-fluoro-2-methoxypyridin-3-yl)pyrrolidin-1-yl)pyridine-2,3-diamine

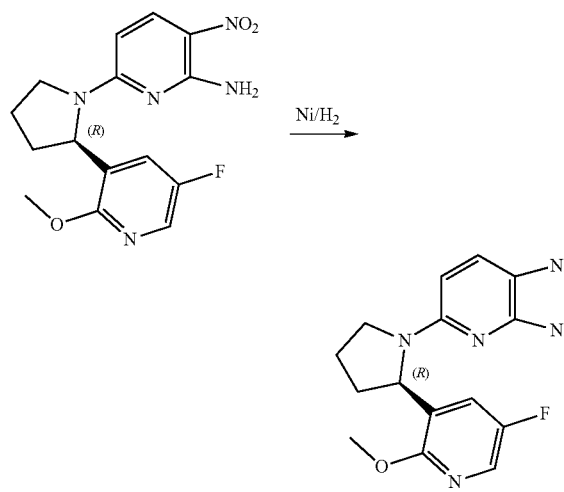

(R)-6-(2-(5-fluoro-2-methoxypyridin-3-yl)pyrrolidin-1-yl)-3-nitropyridin-2-amine (1.65 g, 4.94 mmol) was dissolved in methanol (20 mL), raney nickel (1 g) was added, and the mixture was reacted for 16 hrs at 20° C. under hydrogen atmosphere. The reaction mixture was filtered and concentrated by rotary evaporation, and the residue was used directly in the next step.

LC-MS (M/e): 304.1 (M+H$^+$)

3. Preparation of (R)-5-(2-(5-fluoro-2-methoxypyridin-3-yl)pyrrolidin-1-yl)-3H-imidazo[4,5-b]pyridine

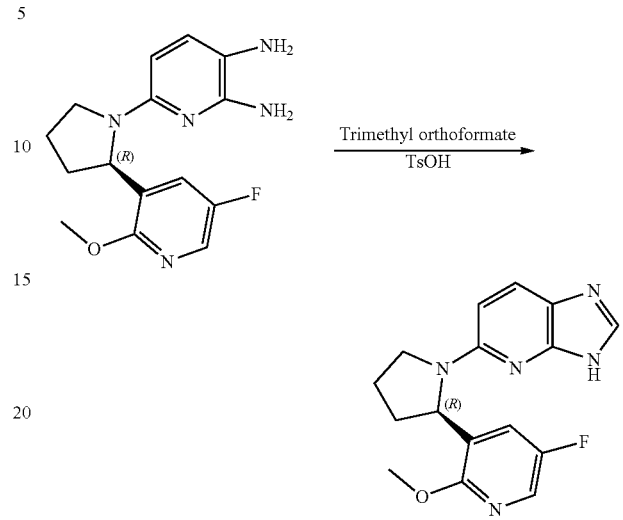

(R)-6-(2-(5-fluoro-2-methoxypyridin-3-yl)pyrrolidin-1-yl)pyridine-2,3-diamine (crude product from the above step, about 3.0 mmol) was dissolved in toluene (30 mL), trimethyl orthoformate (5.2 g, 49 mmol) and p-toluenesulfonic acid (170 mg, 0.99 mmol) were added, and the mixture was heated to 110° C. and reacted for 5 hrs. The reaction mixture was concentrated by rotary evaporation, added with a sodium bicarbonate solution (100 mL) and ethyl acetate (100 mL), and separated, and the aqueous phase was extracted with ethyl acetate (50 mL×3). The organic phase was combined, concentrated by rotary evaporation and purified by column chromatography (ethyl acetate) to give the target product (1.5 g, yield: 96.8%).

LC-MS (M/e): 314.1 (M+H$^+$)

4. Preparation of (R)-3-(1-(3H-imidazo[4,5-b]pyridin-5-yl)pyrrolidin-2-yl)-5-fluoropyridin-2-ol

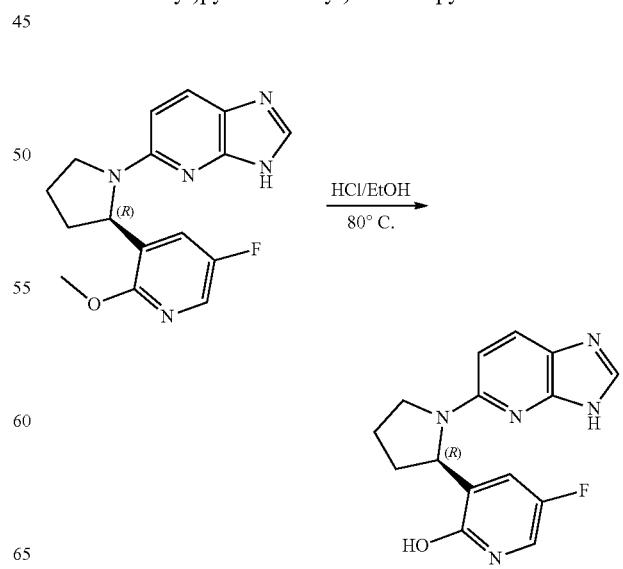

(R)-5-(2-(5-fluoro-2-methoxypyridin-3-yl)pyrrolidin-1-yl)-3H-imidazo[4,5-b]pyridine (1.5 g, 4.79 mmol) was added to a solution of hydrogen chloride in ethanol (30 mL), and the mixture was heated to 90° C. and reacted for 16 hrs. The reaction mixture was concentrated by rotary evaporation, adjusted pH to alkaline with the addition of triethylamine (5 mL), concentrated by rotary evaporation again, and purified by column chromatography (dichloromethane:methanol=10:1) to give the target product (1.4 g, yield: 97.9%).

LC-MS (M/e): 300.1 (M+H⁺)

5. Preparation of tert-butyl ((R)-1-((3-((R)-1-(3H-imidazo[4,5-b]pyridin-5-yl)pyrrolidin-2-yl)-5-fluoropyridin-2-yl)oxy)propan-2-yl)carbamate

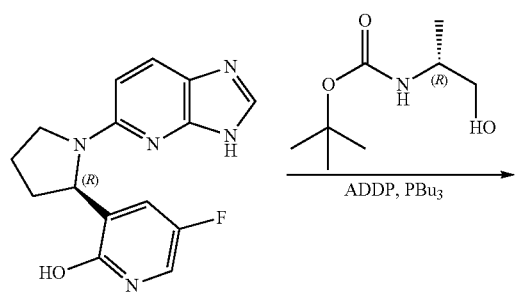

(R)-3-(1-(3H-imidazo[4,5-b]pyridin-5-yl)pyrrolidin-2-yl)-5-fluoropyridin-2-ol (700 mg, 2.34 mmol), tert-butyl (R)-(1-hydroxypropan-2-yl)carbamate (410 mg, 2.34 mmol) and tri-n-butylphosphine (945 mg, 4.68 mmol) were dissolved in tetrahydrofuran (10 mL), and azobisformyl dipiperidine (1.18 g, 4.68 mmol) was added under nitrogen atmosphere, and the mixture was reacted at 30° C. for 2 hrs. The reaction mixture was concentrated, and purified by C18 column chromatography to give the target product (500 mg, yield: 46.7%).

LC-MS (M/e): 457.0 (M+H⁺)

6. Preparation of (R)-1-((3-((R)-1-(3H-imidazo[4,5-b]pyridin-S-yl)pyrrolidin-2-yl)-5-fluoropyridin-2-yl)oxy)propan-2-amine Tert-butyl ((R)-1-((3-((R)-1-(3H-imidazo[4,5-b]pyridin-5-yl)pyrrolidin-2-yl)-5-fluoropyridin-2-yl) oxy)propan-2-yl) carbamate (500 mg, 1.1 mmol) was dissolved in dichloromethane (20 mL), trifluoroacetic acid (20 mL) was added, and the mixture was reacted at 20° C. for 16 hrs. The reaction solution was concentrated, adjusted pH to alkaline with triethylamine, concentrated by rotary evaporation, and purified by C18 column chromatography to give the target product (crude, 400 mg).

LC-MS (M/e): 357.0 (M+H⁺)

7. Preparation of (2²R,6R)-3⁵-fluoro-6-methyl-1³H-4-oxa-7-aza-1(5,3)-imidazo[4,5-b]pyridina-3(3,2)-pyridina-2(1,2)-pyrrolidinacyclooctaphan-8-one (Compound 3')

-continued

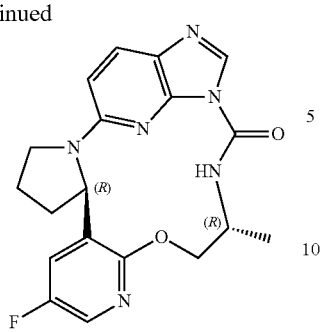

(R)-1-((3-((R)-1-(3H-imidazo[4,5-b]pyridin-5-yl)pyrrolidin-2-yl)-5-fluoropyridin-2-yl)oxy)propan-2-amine (crude product from the above step, 400 mg, about 1.1 mmol) was dissolved in xylene (50 mL), carbonyldiimidazole (535 mg, 3.3 mmol) was added, and the mixture was warmed to 130° C. and reacted for 2 hrs. The reaction mixture was concentrated, purified by column chromatography (petroleum ether:ethyl acetate=1:1) to give the target product (crude, 300 mg), and further separated by HPLC high-pressure reversed-phase preparative chromatography (acetonitrile:water=10%-70%) to give the title compound (100 mg, yield: 23.8%).

Molecular formula: $C_{19}H_{19}FN_6O_2$

Molecular weight: 382.4

LC-MS (M/e): 383.2 (M+H$^+$)

$^1$H-NMR (400 MHz, CDCl$_3$) δ 10.50 (m, 1H), 8.36 (s, 1H), 7.86-7.90 (m, 2H), 7.31-7.35 (m, 1H), 6.51 (d, J=8.8 Hz, 1H), 5.63-5.60 (m, 1H), 5.13-5.17 (m, 1H), 4.39-4.42 (m, 1H), 4.15-4.19 (m, 1H), 3.92-3.98 (m, 1H), 3.65-3.60 (m, 1H), 2.50-2.59 (m, 2H), 2.40-2.50 (m, 1H), 1.95-2.01 (m, 1H), 1.57 (d, J=6.8 Hz, 3H).

The compound 3 and the compound 3' were the same compound, which was confirmed by methods including hydrogen spectrum, mass spectrum, HPLC, specific rotation and the like.

Example 6: ($2^2$R,6S)-$3^5$-fluoro-6-methyl-$1^3$H-4-oxa-7-aza-1(5,3)-imidazo[4,5-b]pyridina-3(3,2)-pyridina-2(1,2)-pyrrolidinacyclooctaphan-8-one (Compound 2')

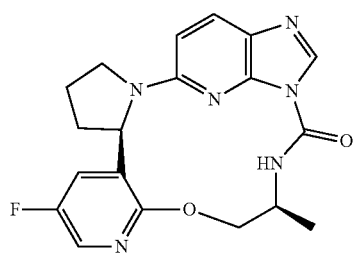 [SMILES: C[C@H]1COc2ncc(F)cc2[C@H]2CCCN2c2ccc3ncn(c3n2)C(=O)N1]

The preparation thereof was the same as in Example 5 except that tert-butyl (S)-(1-hydroxypropan-2-yl)carbamate was used in place of tert-butyl (R)-(1-hydroxypropan-2-yl)carbamate in the step 5.

The compound 2 and the compound 2' were the same compound, which was confirmed by methods including hydrogen spectrum, mass spectrum, HPLC, specific rotation and the like.

Example 7: ($2^2$R,6R)-$3^5$-fluoro-6-methyl-$1^3$H-7-aza-1(5,3)-imidazo[4,5-b]pyridina-3(3,2)-pyridina-2(1,2)-pyrrolidinacyclooctaphan-8-one (Compound 11')

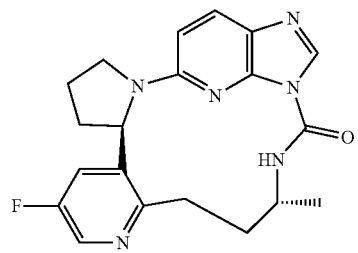 [SMILES: C[C@@H]1CCc2ncc(F)cc2[C@H]2CCCN2c2ccc3ncn(c3n2)C(=O)N1]

1. Preparation of (R)-6-(2-(S-fluoro-2-methoxypyridin-3-yl)pyrrolidin-1-yl)-3-nitropyridin-2-amine

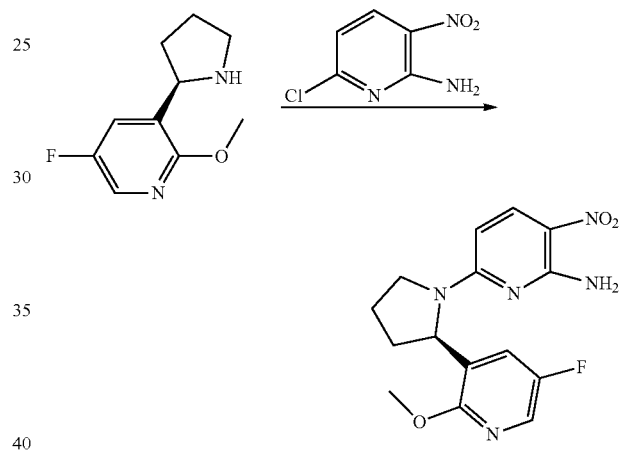

(R)-5-fluoro-2-methoxy-3-(pyrrolidin-2-yl)pyridine (2.0 g, 10.2 mmol) and 6-chloro-3-nitropyridin-2-amine (1.8 g, 10.4 mmol) were added to acetonitrile (50 mL), diisopropylethylamine (3.9 g, 30.2 mmol) was added, and the mixture was heated to 70° C. for 16 hrs. The reaction mixture was concentrated by rotary evaporation, added with water (50 mL), and filtered. The solid was washed with ethyl acetate (30 mL) and dried under vacuum to give the target product (3.27 g, yield: 96.2%).

LC-MS (M/e): 334.1 (M+H$^+$)

2. Preparation of (R)-6-(2-(5-fluoro-2-methoxypyridin-3-yl)pyrrolidin-1-yl)pyridine-2,3-diamine

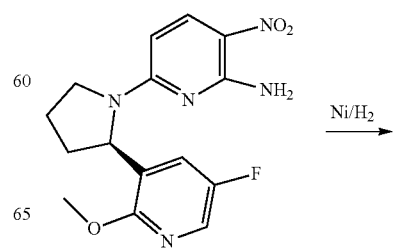

-continued

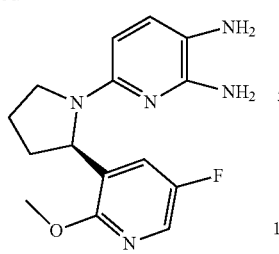

(R)-6-(2-(5-fluoro-2-methoxypyridin-3-yl)pyrrolidin-1-yl)-3-nitropyridin-2-amine (3.27 g, 9.8 mmol) was dissolved in methanol (50 mL), raney nickel (2 g) was added, and the mixture was reacted for 3 hrs at 20° C. under hydrogen atmosphere. The reaction mixture was filtered and concentrated by rotary evaporation, and the residue was used directly in the next step.

LC-MS (M/e): 304.1 (M+H$^+$)

3. Preparation of (R)-5-(2-(S-fluoro-2-methoxypyridin-3-yl)pyrrolidin-1-yl)-3H-imidazo[4,5-b]pyridine

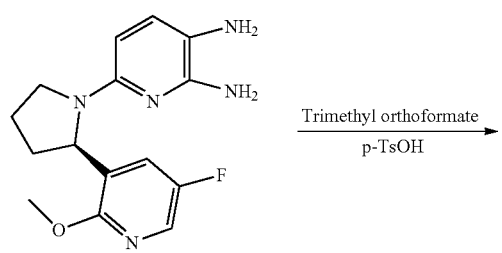

(R)-6-(2-(5-fluoro-2-methoxypyridin-3-yl)pyrrolidin-1-yl)pyridine-2,3-diamine (crude product from the above step, about 9.8 mmol) was dissolved in toluene (100 mL), trimethyl orthoformate (10.4 g, 98 mmol) and p-toluenesulfonic acid (170 mg, 0.99 mmol) were added, and the mixture was heated to 110° C. and reacted for 16 hrs. The reaction mixture was concentrated by rotary evaporation, added with sodium bicarbonate solution (100 mL), and extracted with ethyl acetate (100 mL×3). The organic phase was combined, concentrated by rotary evaporation and purified by column chromatography (petroleum ether:ethyl acetate=1:1) to give the target product (3.05 g, yield: 99.0%).

LC-MS (M/e): 314.1 (M+H$^+$)

4. Preparation of (R)-3-(1-(3H-imidazo[4,5-b]pyridin-5-yl)pyrrolidin-2-yl)-5-fluoropyridin-2-ol

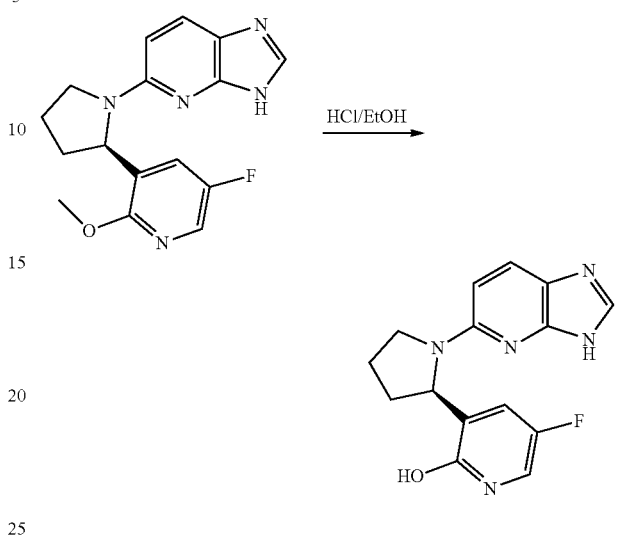

(R)-5-(2-(5-fluoro-2-methoxypyridin-3-yl)pyrrolidin-1-yl)-3H-imidazo[4,5-b]pyridine (3.05 g, 9.7 mmol) was added to a solution of hydrogen chloride in ethanol (100 mL), and the mixture was heated to 80° C. and reacted for 16 hrs. The reaction mixture was concentrated by rotary evaporation, added with triethylamine (5 mL), and concentrated by rotary evaporation again. The reaction mixture was purified by column chromatography (dichloromethane:methanol=10:1) to give the target product (2.8 g, yield: 96.2%).

LC-MS (M/e): 300.1 (M+H$^+$)

5. Preparation of (R)-5-fluoro-3-(1-(3-(((trifluoromethyl)sulfonyl)-3H-imidazo[4,5-b]pyridin-5-yl) pyrrolidin-2-yl)pyridin-2-yl trifluoromethanesulfonate

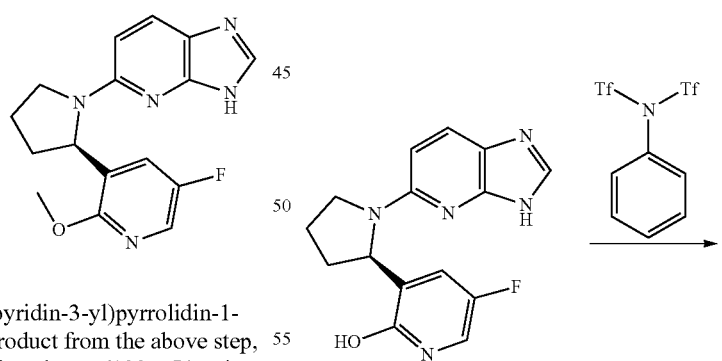

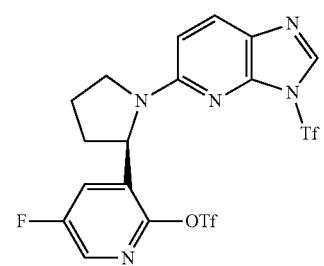

(R)-3-(1-(3H-imidazo[4,5-b]pyridin-5-yl)pyrrolidin-2-yl)-5-fluoropyridin-2-ol (2.8 g, 9.36 mmol) was dissolved in dichloromethane (100 mL), 1,1,1-trifluoro-N-phenyl-N-((trifluoromethyl)sulfonyl) methanesulfonamide (10 g, 28 mmol) and triethylamine (4.7 g, 46.5 mmol) were added, and the mixture was reacted at 20° C. for 16 hrs. The reaction mixture was concentrated by rotary evaporation and purified by column chromatography (petroleum ether:ethyl acetate=5:1) to give the target product (4.46 g, yield: 84.6%).

LC-MS (M/e): 564.0 (M+H$^+$)

6. Preparation of benzyl ((R)-4-(5-fluoro-3-((R)-1-(3-((trifluoromethyl)sulfonyl)-3H-imidazo[4,5-b]pyridin-5-yl)pyrrolidin-2-yl)pyridin-2-yl)-but-3-yn-2-yl)carbamate

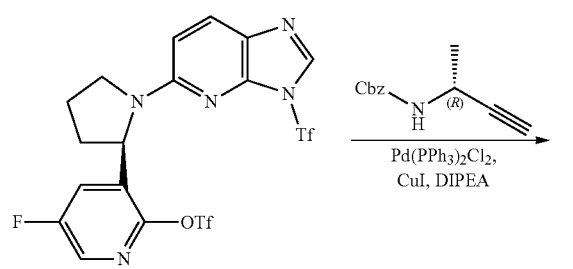

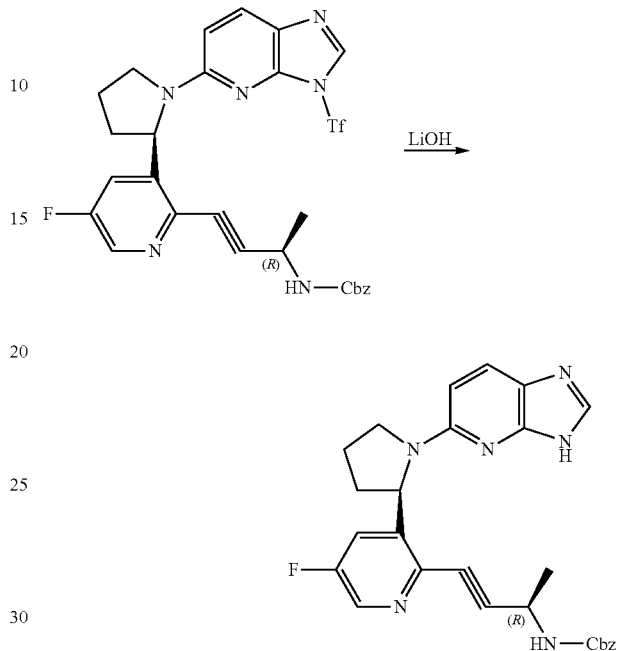

(R)-5-fluoro-3-(1-(3-((trifluoromethyl)sulfonyl)-3H-imidazo[4,5-b]pyridin-5-yl)pyrrolidin-2-yl)pyridin-2-yl trifluoromethanesulfonate (4.46 g, 7.92 mmol), cuprous iodide (300 mg, 1.48 mmol), bis(triphenylphosphine)palladium dichloride (560 mg, 0.8 mmol) and DIPEA (3.0 g, 23.2 mmol) were dissolved in tetrahydrofuran (100 mL), and the mixture was reacted for 0.5 hr at 50° C. under nitrogen atmosphere. A solution of benzyl (R)-but-3-yn-2-yl carbamate (1.6 g, 7.9 mmol) in tetrahydrofuran was added slowly, and the mixture was reacted at 50° C. for 5 hrs. The reaction mixture was concentrated by rotary evaporation and purified by column chromatography (petroleum ether:ethyl acetate=2:1) to give the target product (3.7 g, yield: 75.8%).

LC-MS (M/e): 617.2 (M+H$^+$)

7. Preparation of benzyl ((R)-4-(3-((R)-1-(3H-imidazo[4,5-b]pyridin-5-yl)pyrrolidin-2-yl)-5-fluoropyridin-2-yl)-but-3-yn-2-yl)carbamate Benzyl ((R)-4-(5-fluoro-3-((R)-1-(3-((trifluoromethyl)sulfonyl)-3H-imidazo[4,5-b]pyridin-5-yl) pyrrolidin-2-yl) pyridin-2-yl)-but-3-yn-2-yl)carbamate (3.7 g, 6.0 mmol) was dissolved in tetrahydrofuran (40 mL) and water (10 mL), lithium hydroxide (1.26 g, 30 mmol) was added, and the mixture was reacted at 20° C. for 2 hrs. The reaction mixture was added with ethyl acetate (100 mL) and water (50 mL) and separated, and the aqueous phase was extracted with ethyl acetate (50 mL×2). The organic phase was combined, concentrated and purified by column chromatography (dichloromethane:methanol=20:1) to give the target product (2.6 g, yield: 89.6%).

LC-MS (M/e): 485.2 (M+H$^+$)

8. Preparation of (R)-4-(3-((R)-1-(3H-imidazo[4,5-b]pyridin-5-yl)pyrrolidin-2-yl)-5-fluoropyridin-2-yl)-butan-2-amine

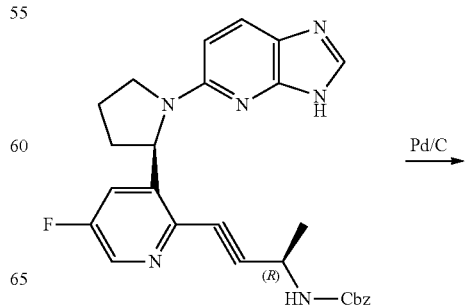

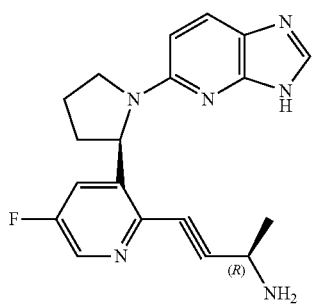

Benzyl ((R)-4-(3-((R)-1-(3H-imidazo[4,5-b]pyridin-5-yl)pyrrolidin-2-yl)-5-fluoropyridin-2-yl)-but-3-yn-2-yl)carbamate (1 g, 2.1 mmol) was dissolved in methanol (50 mL), Palladium on Carbon (500 mg) was added, and the mixture was reacted for 16 hrs at 20° C. under hydrogen atmosphere. The reaction mixture was filtered, the filtrate was concentrated to give the target product (crude, 700 mg) which was used directly in the next step without purification.

LC-MS (M/e): 335.2 (M+H$^+$)

9. Preparation of (2$^2$R,6R)-3$^5$-fluoro-6-methyl-1$^3$H-7-aza-1(5,3)-imidazo[4,5-b]pyridina-3(3,2)-pyridina-2(1,2)-pyrrolidinacyclooctaphan-8-one (Compound 119)

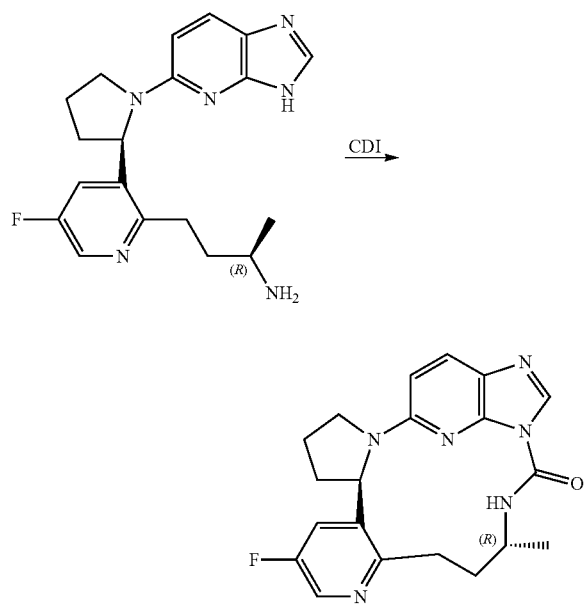

N,N-carbonyldiimidazole (412 mg, 2.54 mmol) was dissolved in xylene (25 mL), and then a solution of (R)-4-(3-((R)-1-(3H-imidazo[4,5-b]pyridin-5-yl)pyrrolidin-2-yl)-5-fluoropyridin-2-yl)-butan-2-amine (crude, 300 mg, about 0.85 mmol) in xylene (25 mL) was added, and the mixture was reacted at 20° C. for 2 hrs, warmed to 130° C. and reacted for 5 hrs. The reaction mixture was concentrated, purified by column chromatography (petroleum ether:ethyl acetate=1:1) to give the target product (crude), and separated by HPLC high-pressure preparative chromatography (acetonitrile:water=10%-80%) to give the title compound (70 mg, yield: 21.7%).

Molecular formula: $C_{20}H_{21}FN_6O$

Molecular weight: 380.4

LC-MS (M/e): 381.1 (M+H$^+$)

$^1$H-NMR (400 MHz, CDCl$_3$) δ 9.48 (d, J=8.4 Hz, 1H), 8.35 (s, 1H), 8.31 (d, J=2.4 Hz, 1H), 7.89 (d, J=8.8 Hz, 1H), 7.15 (dd, J$_1$=2.4 Hz, J$_2$=9.6 Hz, 1H), 6.55 (d, J=8.8 Hz, 1H), 5.43 (t, J=6.4 Hz, 1H), 4.34-4.37 (m, 1H), 3.93-3.99 (m, 1H), 3.68-3.74 (m, 1H), 3.40-3.47 (m, 1H), 2.86-2.98 (m, 2H), 2.50-2.57 (m, 1H), 2.36-2.41 (m, 1H), 2.17-2.27 (m, 2H), 1.87-1.98 (m, 1H), 1.82-1.89 (m, 1H), 1.40 (d, J=6.8 Hz, 3H).

The compound 11 and the compound 11' were the same compound, which was confirmed by methods including hydrogen spectrum, mass spectrum, HPLC, specific rotation and the like.

Activity Assay

Exemplary activity assay for some compounds of the present invention are provided hereinafter to show the beneficial activity and beneficial technical effect of the compound of the present invention. However, it should be understood that the following experimental schemes are only illustrations for the present invention rather than limit the scope of the present invention.

Experimental Example 1: In Vitro Cytological Inhibitory Activity of Compounds of the Present Invention Experimental Materials The test compounds were compounds in the examples above.

The cell lines used in the experiment have the following meanings: Ba/F3 LMNA-NTRK1-G595R cell line:
  a stable expression cell line of Ba/F3 cells transfected with LMNA-NTRK1 G595R; Ba/F3 ETV6-NTRK3-G623R cell line:
  a stable expression cell line of Ba/F3 cells transfected with ETV6-NTRK3-G623R.

Experimental Method (CelltiterGlo Assay)

1. Cell Culture and Inoculation

All cells were suspension cells and the medium was RPMI-1640+10% FBS, and cells were tested in a logarithmic growth phase.

Cells in the logarithmic growth phase were collected and counted using a platelet counter. The cell viability was detected by the trypan blue exclusion method, and the cell viability was kept over 90%. The cell concentration was adjusted to be in a proper range; 90 μL of the cell suspension was added to a 96-well plate.

TABLE 1

| Number of cell inoculation | |
|---|---|
| Cell lines | Number of cells inoculated |
| Ba/F3 LMNA-NTRK1-G595R | 3000 cells/well |
| Ba/F3 ETV6-NTRK3-G623R | 3000 cells/well |

2. Preparation of Test Compounds
2.1 Preparation of DMSO Stock Solutions of Test Compounds, See Table 2 for Concentrations Thereof.

TABLE 2

Stock solution concentration (mM) of test compounds

| Compounds | Stock solution concentration |
|---|---|
| Compound 2 | 10 mM |
| Compound 3 | 10 mM |
| Compound 11 | 10 mM |
| Compound 13 | 10 mM |

2.2 Preparation of Working Stock Solutions of Test Compounds

The stock solutions of test compounds were diluted from 10 mM to 1 mM with DMSO and then serially diluted in a 3-fold gradient for 9 concentrations. The 2 μL DMSO-gradient diluted compound solutions were added to 98 μL culture solutions to give working stock solutions of test compounds (compound concentration was 10-fold higher than the final concentration, DMSO concentration was 1%, maximum concentration was 10 μM).

Maximum concentration was in DMSO solvent control, blank wells were only added with medium without cells inoculated.

2.3 Compound Treatment

10 μL of compound working stock solution was added to each well in the 96-well plate inoculated with cells (10-fold dilution, final DMSO concentration was 0.1%).

The final concentrations of test compounds were: 1000 nM, 333.33 nM, 111.11 nM, 37.04 nM, 12.35 nM, 4.12 nM, 1.37 nM, 0.46 nM and 0.15 nM.

The cells were cultured in a cell culture incubator at 5% $CO_2$ for 72 hrs.

3. Detection

The CTG reagent was thawed and the cell plate was equilibrated to room temperature for 30 mins, 60 μL of reagent (Celltiter Glo assay kit) was added to each well, shaking was performed for 2 mins with a shaker (in the absence of light), and the plate was incubated at room temperature for 10 mins (in the absence of light). The light signal values were read on the multi-functional microplate reader.

4. Data Processing

1) Inhibition (%)=(DMSO solvent control well reading−test compound well reading)/(DMSO solvent control well reading−blank well reading)×100%;
2) a curve was plotted with GraphPad Prism 5.0 and $IC_{50}$ was obtained.

Experimental Result and Conclusion

TABLE 3

In vitro cytological activity ($IC_{50}$, nM) of compounds of the present invention

| Test compounds | Ba/F3 LMNA-NTRK1-G595R(nM) | Ba/F3 ETV6-NTRK3-G623R(nM) |
|---|---|---|
| Compound 2 | 0.6 | 1 |
| Compound 3 | 0.6 | 1 |
| Compound 11 | 2 | 1.9 |
| Compound 13 | 17.3 | 18.9 |

It can be seen from Table 3 that the compounds of the present invention can effectively inhibit the proliferation of cells such as Ba/F3 LMNA-NTRK1-G595R and Ba/F3 ETV6-NTRK3-G623R, indicating that the compounds of the present invention have the potential of clinical application in treating drug-resistant cancerous diseases caused by NTRK gene mutation.

Experimental Example 2: In Vitro Cytological Inhibitory Activity of Compounds of the Present Invention

EXPERIMENTAL MATERIALS

The test compounds were compounds in the examples above.

The cell lines used in the experiment have the following meanings:

Ba/F3 SLC34A2/ROS1-G2032R cell line:
    a stable expression cell line of Ba/F3 cells transfected with SLC34A2/ROS1-G2032R.

Experimental Method (Celltiter-Glo Assay)
1. Cell Culture and Inoculation

All cells were suspension cells and the medium was RPMI-1640+10% FBS, and cells were tested in a logarithmic growth phase.

Cells in the logarithmic growth phase were collected and counted using a platelet counter. The cell viability was detected by the trypan blue exclusion method, and the cell viability was kept over 90%. The cell concentration was adjusted to be in a proper range; 90 μL of the cell suspension was added to a 96-well plate.

TABLE 4

Number of cell inoculation

| Cell lines | Number of cells inoculated |
|---|---|
| Ba/F3 SLC34A2/ROS1-G2032R | 3000 cells/well |

2. Preparation of Test Compounds
2.1 Preparation of DMSO Stock Solutions of Test Compounds, See Table 5 for Concentrations Thereof.

TABLE 5

Stock solution concentration (mM) of test compounds

| Compounds | Stock solution concentration |
|---|---|
| Compound 3 | 10 mM |
| Compound 11 | 10 mM |
| Compound 13 | 10 mM |

2.2 Preparation of Working Stock Solutions of Test Compounds

The stock solutions of test compounds were diluted from 10 mM to 1 mM with DMSO and then serially diluted in a 3.16-fold gradient for 9 concentrations. The 2 μL DMSO-gradient diluted compound solutions were added to 98 μL culture solutions to give working stock solutions of test compounds (compound concentration was 10-fold higher than the final concentration, DMSO concentration was 1%, maximum concentration was 10 μM).

Maximum concentration was in DMSO solvent control, blank wells were only added with medium without cells inoculated.

2.3 Compound Treatment

10 μL of compound working stock solution was added to each well in the 96-well plate inoculated with cells (10-fold dilution, final DMSO concentration was 0.1%).

The final concentrations of test compounds were: 1000 nM, 316 nM, 100 nM, 31.6 nM, 10 nM, 3.16 nM, 1 nM, 0.316 nM and 0.1 nM.

The cells were cultured in a cell culture incubator at 5% $CO_2$ for 72 hrs.

3. Detection

The CTG reagent was thawed and the cell plate was equilibrated to room temperature for 30 mins, 100 μL of reagent (Celltiter Glo assay kit) was added to each well, shaking was performed for 5 mins with a shaker (in the absence of light), and the plate was incubated at room temperature for 20 mins (in the absence of light). The light signal values were read on the multi-functional microplate reader.

4. Data Processing
1) Cell viability (%)=(test compound well reading−blank well reading)/(DMSO solvent control well reading−blank well reading)×100%;
2) a curve was plotted with GraphPad Prism 5.0 and $IC_{50}$ was obtained.

Experimental result and conclusion

TABLE 6

| Test compounds | In vitro cytological activity ($IC_{50}$, nM) of compounds of the present invention Ba/F3 SLC34A2/ROS1-G2032R |
|---|---|
| Compound 3 | 2.3 |
| Compound 11 | 4.2 |
| Compound 13 | 6.7 |

It can be seen from Table 6 that the compounds of the present invention can effectively inhibit the proliferation of cells such as Ba/F3 SLC34A2/ROS1-G2032R, indicating that the compounds of the present invention have the potential of clinical application in treating drug-resistant cancerous diseases caused by ROS gene mutation.

Experimental Example 3: Efficacy Study Experiment in Compound of the Present Invention on BaF3-LMNA-NTRK1-G595R Stable Cell Strain Subcutaneous Xenograft Model Experimental Materials The test compounds were compounds in the examples above.

Positive control: compound LOXO-195 with a structure shown as follows, prepared according to a prior art method (see patent application WO2011146336):

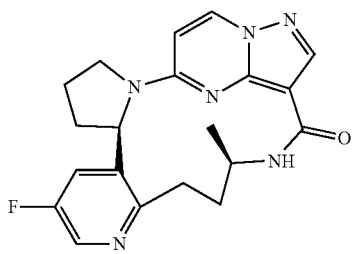 [SMILES: C[C@@H]1CCc2ncc(F)cc2[C@H]2CCCN2c2ccn3ncc(c3n2)C(=O)N1]

Experimental Method 1.1 Cell Inoculation

The RPMI 1640 serum-free medium resuspended BaF3 LMNA-NTRK1-G595R stable cell strains were inoculated subcutaneously in the right scapular region of mice (NOD-SCID) at $1×10^6$ cells/mouse (0.1 mL/mouse).

1.2 Administration in Groups

When the average tumor volume was around 500 $mm^3$, the groups were randomized into vehicle group, Compound 3 group (10 mg/kg, 5 mg/kg, 3 mg/kg, 1 mg/kg, bid) and LOXO-195 group (30 mg/kg, 10 mg/kg, 3 mg/kg, bid).

For the detailed administration method, administration dosage and administration route, see Table 7-1 and Table 7-2.

TABLE 7-1

Efficacy experiment 1 inBaF3 LMNA-NTRK1-G595R model

| Group | n | Administered group | Dose (mg/Kg) | Administration route | Administration time |
|---|---|---|---|---|---|
| 1 | 6 | Vehicle group | — | — | — |
| 2 | 6 | LOXO-195 group | 3 | p.o., bid | 7 days |
| 3 | 6 | LOXO-195 group | 10 | p.o., bid | 7 days |
| 4 | 6 | Compound 3 | 3 | p.o., bid | 7 days |

Note:
n was the number of animals; the drug was administered on the day of grouping.

TABLE 7-2

Efficacy experiment 2 in BaF3 LMNA-NTRK1-G595R model

| Group | n | Administered group | Dose (mg/Kg) | Administration route | Administration time |
|---|---|---|---|---|---|
| 5 | 6 | LOXO-195 group | 30 | p.o., bid | 7 days |
| 6 | 6 | Compound 3 | 1 | p.o., bid | 7 days |
| 7 | 6 | Compound 3 | 5 | p.o., bid | 7 days |
| 8 | 6 | Compound 3 | 10 | p.o., bid | 7 days |

Note:
n was the number of animals; the drug was administered on the day of grouping.

1.3 Experimental Evaluation Index
1) Tumor growth inhibition ratio TGI (%)

$$TGI(\%)=(1-T/C)×100\%$$

2) Tumor volume ratio T/C (%) (treatment group/control group)

$$T/C(\%)=T_{RTV}/C_{RTV}×100\%$$

$RTV=V_t/V_0$, where $V_t$ was the tumor volume on day t after grouping, $V_0$ was the tumor volume on the day of grouping;

$T_{RTV}$: average relative tumor volume of the administered group; $C_{RTV}$: average relative tumor volume of the solvent control group.

3) The efficacy evaluation standard was as follows: ineffective when T/C (%) was more than 40%, and effective when the T/C (%) was less than or equal to 40%; effective when TGI was more than or equal to 60%.

Experimental Result and Conclusion

TABLE 8-1

Inhibition of Experiment 1 on BaF3-LMNA-NTRK1-G595R stable cell strain xenograft tumor

| Group | Dosage (mg/Kg) | T/C (%) | TGI (%) |
|---|---|---|---|
| 1 (Vehicle group) | — | — | — |
| 2 (LOXO-195 group) | 3, bid | 93.6 | 6.4 |
| 3 (LOXO-195 group) | 10, bid | 63.1 | 36.9 |
| 4 (Compound 3 group) | 3, bid | 73.2 | 26.8 |

TABLE 8-2

Inhibition of Experiment 2 on BaF3-LMNA-NTRK1-G595R stable cell strain xenograft tumor

| Group | Dosage (mg/Kg) | T/C (%) | TGI (%) |
|---|---|---|---|
| 5 (LOXO-195 group) | 30, bid | 0 | 100 |
| 6 (Compound 3 group) | 1, bid | 53.7 | 46.3 |
| 7 (Compound 3 group) | 5, bid | 0 | 100 |
| 8 (Compound 3 group) | 10, bid | 0 | 100 |

Experimental data show that oral administration of an effective amount of compound of the present invention can obviously inhibit a cell line BaF3-LMNA-NTRK1-G595R tumor efficacy model containing NTRK fusion genes, which means that the compound of the present invention shows good tumor inhibition effect on tumors with NTRK fusion gene mutation, and has a good clinical application prospect.

The invention claimed is:

1. A compound of general formula (IV) or a pharmaceutically acceptable salt, ester or stereoisomer thereof,

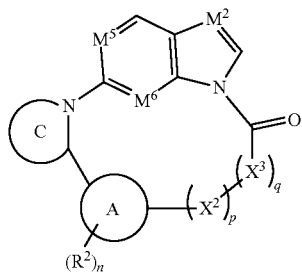

IV wherein:
$M^2$ is N; $M^6$ is N; $M^5$ is CH;
ring C is pyrrolidinyl or piperidinyl optionally, each one of which is substituted with a substituent selected from: $R^4$, $R^5$, $R^6$, halogen, amino, hydroxy, $C_{1-4}$ alkyl, $C_{1-4}$ alkoxy, $C_{1-4}$ alkylamino, di($C_{1-4}$ alkyl)amino, halo $C_{1-4}$ alkyl, hydroxy $C_{1-4}$ alkyl, amino $C_{1-4}$ alkyl and halo $C_{1-4}$ alkoxy;
—$(X^2)_p$— is —$C(R^5)(R^6)$—, —$C(R^5)(R^6)$—$C(R^5)(R^6)$— or —O—$C(R^5)(R^6)$, and the left chemical bond thereof is connected to ring A and the right chemical bond thereof is connected to $X^3$;
—$(X^3)_q$— is —$C(R^5)(R^6)$—$C(R^5)(R^6)$—, —$C(R^5)(R^6)$—$N(R^4)$— or —$C(R^5)(R^6)$—O—, and the left chemical bond thereof is connected to $X^2$ and the right chemical bond thereof is connected to carbonyl;

ring A is selected from phenyl and 5-6 membered monoheteroaryl;
$R^2$, when present, is independently selected from hydrogen, halogen and the following groups optionally substituted with 1 to 3 $Q^1$: $C_{1-4}$ alkyl, —$OR^a$ and —$NR^aR^b$; $Q^1$, when present, is independently selected from hydroxy, amino, halogen, nitro, cyano, $C_{1-4}$ alkyl, $C_{1-4}$ alkoxy, $C_{1-4}$ alkylamino, di($C_{1-4}$ alkyl)amino, halo $C_{1-4}$ alkyl, hydroxy $C_{1-4}$ alkyl, amino $C_{1-4}$ alkyl and halo $C_{1-4}$ alkoxy;
$R^a$ and $R^b$, when present, are each independently selected from hydrogen and $C_{1-4}$ alkyl;
$R^5$ and $R^6$, when present, are each independently selected from hydrogen, halogen, hydroxy, amino, $C_{1-4}$ alkyl and $C_{1-4}$ alkoxy;
$R^4$, when present, is independently selected from hydrogen and $C_{1-4}$ alkyl optionally substituted with 1 to 2 $Q^2$; $Q^2$, when present, is independently selected from hydroxy, amino, halogen and $C_{1-4}$ alkoxy; and
n is 0, 1 or 2.

2. The compound or the pharmaceutically acceptable salt, ester or stereoisomer thereof according to claim 1, wherein:
ring C pyrrolidinyl;
ring A is selected from phenyl, pyrrolyl, imidazolyl, pyrazolyl, oxazolyl, isoxazolyl, thiazolyl, isothiazolyl, 1,2,4-triazolyl, 1,2,3-triazolyl, 1,3,4-oxadiazolyl, 1,2,4-oxadiazolyl, 1,3,4-thiadiazolyl, 1,2,4-thiadiazolyl, pyridinyl, pyrimidinyl, pyridazinyl, 1,3,5-triazinyl and tetrazinyl;
$R^2$, when present, is independently selected from hydrogen, fluorine, chlorine, bromine, iodine, hydroxy, amino, methyl, ethyl, propyl, isopropyl, butyl, isobutyl, sec-butyl, methylamino, dimethylamino, ethylamino, diethylamino, methoxy, ethoxy, propoxy, isopropoxy, trifluoromethyl and trifluoromethoxy;
$R^5$ and $R^6$, when present, are each independently selected from hydrogen, fluorine, chlorine, bromine, iodine, hydroxy, amino, methyl, ethyl, propyl, isopropyl, butyl, isobutyl, sec-butyl, methoxy, ethoxy, propoxy and isopropoxy; and
$R^4$, when present, is independently selected from hydrogen, methyl, ethyl, propyl, isopropyl, butyl, isobutyl and sec-butyl.

3. The compound or the pharmaceutically acceptable salt, ester or stereoisomer thereof according to claim 1, wherein:
ring A is selected from

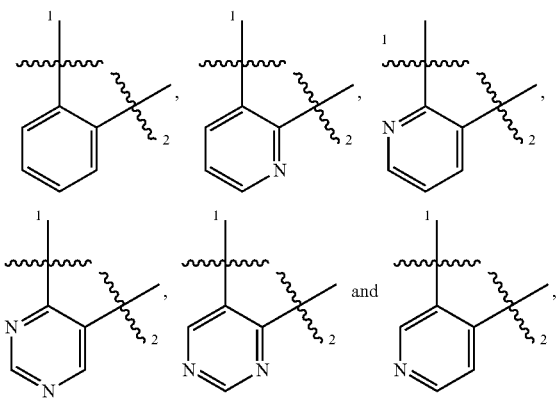

and the wavy line marked with "1" represents the connection point of ring A to L$^1$ and the wavy line marked with "2" represents the connection point of ring A to X$^2$;

- —(X$^2$)$_p$— is selected from —CH$_2$—, —CH$_2$ and —O—CH$_2$—, and the left chemical bond thereof is connected to ring A and the right chemical bond thereof is connected to X$^3$;
- —(X$^3$)$_q$— is selected from —CH(R$^6$)—N(R$^4$)— and —CH(R$^6$)—O—, and the left chemical bond thereof is connected to X$^2$ and the right chemical bond thereof is connected to carbonyl; and R$^6$, when present, is hydrogen or C$_{1-4}$ alkyl;

R$^4$, when present, is hydrogen or C$_{1-4}$ alkyl.

4. The compound or the pharmaceutically acceptable salt, ester or stereoisomer thereof according to claim 1, wherein the compound is selected from the following compounds:

| No. | Compound |
|---|---|
| Compound 1 | |
| Compound 2 | |
| Compound 2-1 | |
| Compound 3 | |
| Compound 3-1 | |
| Compound 4 | |
| Compound 5 | |
| Compound 6 | |
| Compound 7 | |
| Compound 8 | |

| No. | Compound |
|---|---|
| Compound 9 | (structure) |
| Compound 10 | (structure) |
| Compound 11 | (structure) |
| Compound 11-1 | (structure) | wherein * represents that a carbon atom is a chiral carbon atom having a single configuration (R configuration or S configuration).

5. The compound or the pharmaceutically acceptable salt, ester or stereoisomer thereof according to claim 4, wherein the compound is selected from:

| No. | Compound |
|---|---|
| Compound 2' | (structure) |
| Compound 3' | (structure) |
| Compound 11' | (structure) |

6. A pharmaceutical formulation comprising the compound or the pharmaceutically acceptable salt, ester or stereoisomer thereof according to claim 1, and one or more pharmaceutically acceptable carriers and/or excipients.

7. A pharmaceutical composition comprising the compound or the pharmaceutically acceptable salt, ester or stereoisomer thereof according to claim 1, and one or more second therapeutically active agents selected from:

a drug for the treatment of pain, which is selected from Nav1.7 channel modulators, opioid analgesics, non-steroidal anti-inflammatory drugs, sedatives, selective/non-selective cyclooxygenase inhibitors, antiepileptics, antidepressants, local anesthetics, 5-HT receptor blockers, 5-HT receptor agonists, ergot alkaloids, β-receptor blockers, M receptor blockers, nitrates and vitamin K;

a drug for the treatment of cancer, which is selected from mitotic inhibitors, alkylating agents, antimetabolites, antisense DNA or RNA, antitumor antibiotics, growth factor inhibitors, signal transduction inhibitors, cell cycle inhibitors, enzyme inhibitors, retinoid receptor modulators, proteasome inhibitors, topoisomerase inhibitors, biological response modifiers, hormones, angiogenesis inhibitors, cell growth inhibitors, targeted antibodies, HMG-CoA reductase inhibitors and prenyl-protein transferase inhibitors;

a drug for the treatment of neurodegenerative diseases, which is selected from dopamine-mimetics, dopamine receptor agonists, agents affecting dopamine metabolism, NMDA receptor antagonists, adenosine A2A receptor inhibitors, agents affecting DA release and reuptake, central anticholinergics, cholinesterase inhibitors, 5-HT agonists, a2 adrenergic receptor antagonists, antidepressants, cholinergic receptor agonists, β/γ secretase inhibitors, H3 receptor antagonists and antioxidant agents;

a drug for the treatment of autoimmune diseases, which is selected from antirheumatic drugs, non-steroidal anti-inflammatory drugs, glucocorticoid drugs, TNF antagonists, cyclophosphamide, mycophenolate mofetil and cyclosporine, which is used for alleviating the disease; and a drug for the treatment of inflammation, which is selected from steroidal anti-inflammatory drugs and non-steroidal anti-inflammatory drugs.

8. A method for preparing the compound of general formula (IV) or the pharmaceutically acceptable salt, ester or stereoisomer thereof,

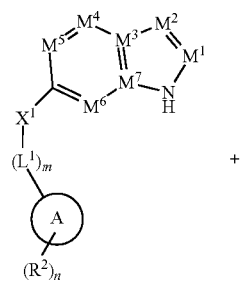

Intermediate 1

+

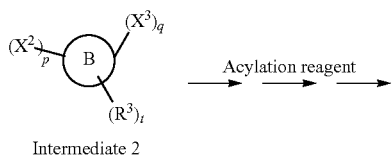

Intermediate 2 → Acylation reagent

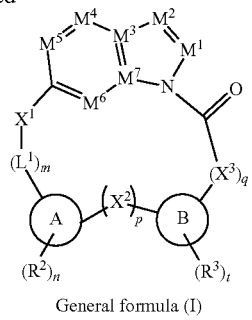

General formula (I)

wherein
$M^1$ is CH: $M^4$ is CH: $M^3$ is C: $M^7$ is C;
$X^1$, together with $L^1$, forms pyrrolidinyl or piperidinyl; optionally, each one of which is substituted with a substituent selected from: $R^4$, $R^5$, $R^6$, halogen, amino, hydroxy, $C_{1-4}$ alkyl, $C_{1-4}$ alkoxy, $C_{1-4}$ alkylamino, di($C_{1-4}$ alkyl)amino, halo $C_{1-4}$ alkyl, hydroxy $C_{1-4}$ alkyl, amino $C_{1-4}$ alkyl and halo $C_{1-4}$ alkoxy;
ring B is absent;
the other substituents and variables are defined as claim 5, and the method comprises the steps as follows:
intermediate 1 and intermediate 2 are subjected to substitution reaction, deprotection reaction, acylation reaction (using an acylation reagent) in the presence of an organic solvent and a catalyst at a proper temperature to obtain the compound of the general formula (I).

9. The compound or the pharmaceutically acceptable salt, ester or stereoisomer thereof according to claim 1, wherein ring A is phenyl or 5-6 membered nitrogen-containing heteroaryl.

10. The compound or the pharmaceutically acceptable salt, ester or stereoisomer thereof according to claim 1, wherein:
$R^6$, when present, is hydrogen or methyl;
$R^4$, when present, is hydrogen or methyl.

* * * * *